US012403046B2

(12) United States Patent
Minami

(10) Patent No.: US 12,403,046 B2
(45) Date of Patent: Sep. 2, 2025

(54) DISPOSABLE WEARING ARTICLE

(71) Applicant: DAIO PAPER CORPORATION, Ehime (JP)

(72) Inventor: Takeshi Minami, Tochigi (JP)

(73) Assignee: Daio Paper Corporation, Ehime (JP)

( * ) Notice: Subject to any disclaimer, the term of this patent is extended or adjusted under 35 U.S.C. 154(b) by 437 days.

(21) Appl. No.: 18/016,405

(22) PCT Filed: Jun. 3, 2021

(86) PCT No.: PCT/JP2021/021253
§ 371 (c)(1),
(2) Date: Jan. 16, 2023

(87) PCT Pub. No.: WO2022/034729
PCT Pub. Date: Feb. 17, 2022

(65) Prior Publication Data
US 2023/0310228 A1     Oct. 5, 2023

(30) Foreign Application Priority Data
Aug. 11, 2020 (JP) ................................. 2020-135901

(51) Int. Cl.
*A61F 13/49* (2006.01)
*A61F 13/496* (2006.01)

(52) U.S. Cl.
CPC ........ *A61F 13/4902* (2013.01); *A61F 13/496* (2013.01); *A61F 2013/49022* (2013.01); *A61F 2013/49031* (2013.01)

(58) Field of Classification Search
CPC .... A61F 13/49; A61F 13/4902; A61F 13/496; A61F 13/51104; A61F 2013/49022; A61F 2013/49031

(Continued)

(56) References Cited

U.S. PATENT DOCUMENTS

2017/0014277 A1    1/2017  Matsui
2021/0077318 A1*   3/2021  Koyama ............... A61F 13/494

FOREIGN PATENT DOCUMENTS

EP      3127517 A1    2/2017
JP      2010200974 A  9/2010

(Continued)

OTHER PUBLICATIONS

Extended European Search Report for European Patent Application No. 21855808.8, dated May 27, 2024.

(Continued)

*Primary Examiner* — Michele Kidwell
(74) *Attorney, Agent, or Firm* — Andrus Intellectual Property Law, LLP

(57) ABSTRACT

A disposable wearing article includes: a waist portion having an outer side portion exposed on an external surface and an inner side portion overlapped with an inner side of the outer side portion; an adjacent portion adjacent to the waist portion; an outer side stretchable region extending over the outer side portion and the waist adjacent portion; and an inner side stretchable region provided in the inner side portion, wherein the outer side portion and the inner side portion are joined with each other in a stripe pattern formed by disposing, alternately and repeatedly in the width direction, inner/outer bonded portions continuous in a front-back direction and inner/outer non-bonded portions continuous in the front-back direction, and a natural length in the width direction of the outer side portion is 1.1 to 1.8 times a natural length in the width direction of the inner side portion.

8 Claims, 24 Drawing Sheets

(58) Field of Classification Search
USPC .............................. 604/385.01, 366, 385.24
See application file for complete search history.

(56) References Cited

FOREIGN PATENT DOCUMENTS

| | | |
|---|---|---|
| JP | 2013-183828 | 9/2013 |
| JP | 2015171503 A | 10/2015 |
| JP | 2015198915 A | 11/2015 |
| JP | 2016154654 A | 9/2016 |
| JP | 2016-187387 | 11/2016 |
| JP | 2017064225 A | 4/2017 |
| JP | 2019-118581 | 7/2019 |

OTHER PUBLICATIONS

International Search Report for PCT/JP2021/021253 dated Aug. 17, 2021.

\* cited by examiner

FIG. 4 (a)
FIG. 4 (b)
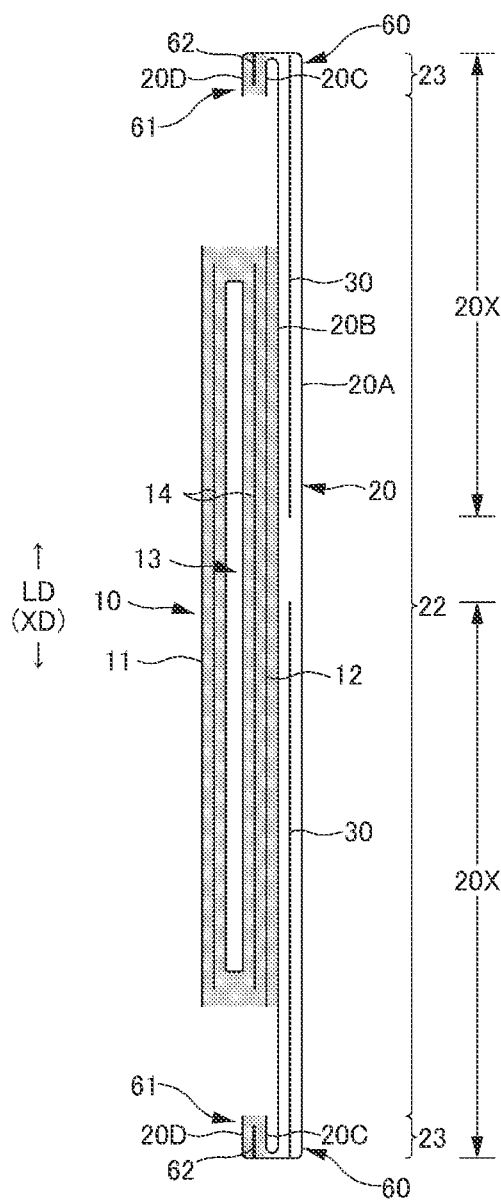
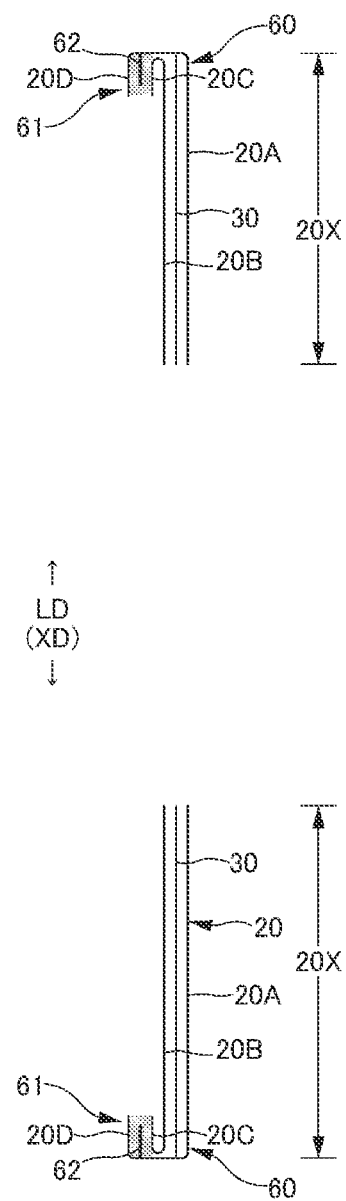

[FIG.20]
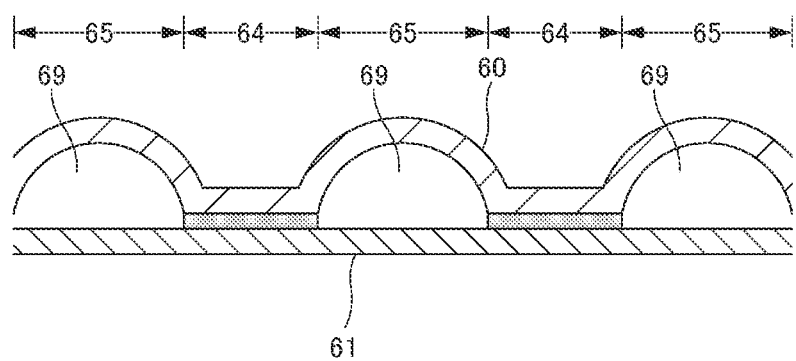

DISPOSABLE WEARING ARTICLE

CROSS-REFERENCE TO RELATED APPLICATIONS

This application is the U.S. national stage application of International Application PCT/JP2021/021253, filed Jun. 3, 2021, which international application was published on Feb. 17, 2022, as International Publication WO 2022/034729 in the Japanese language. The International Application claims priority of Japanese Patent Application No. 2020-135901, filed Aug. 11, 2020. The international application and Japanese application are both incorporated herein by reference, in entirety.

TECHNICAL FIELD

The present invention relates to a disposable wearing article provided with a waist portion elastically stretching and contracting by an elastic film.

BACKGROUND ART

In a disposable wearing article such as a disposable diaper, to improve fitting to a body surface, it is common to impart elasticity to an appropriate place such as around legs or around a waist. As a method of imparting elasticity, a method of attaching an elongated elastic member such as a rubber thread in a state of being stretched in a longitudinal direction has been widely adopted. In this case, in order to impart the elasticity to a region having a certain size of area, it has been also often performed to arrange a plurality of rubber threads at intervals in a direction orthogonal to the longitudinal direction. In addition, as a method of obtaining further excellent surface fitting, a method of attaching an elastic film in a state of being stretched in a direction of imparting elasticity has been proposed (for example, see Patent Literature 1.)

A stretchable region including this elastic film is obtained when the elastic film is stacked between a first sheet layer and a second sheet layer, and, in a state in which the elastic film is stretched in a stretchable direction, the first sheet layer and the second sheet layer are welded by a plurality of dotted sheet joined portions arranged at intervals in the stretchable direction and a direction orthogonal thereto through joint holes formed in the elastic film. Further, in this stretchable region, in a natural length state, as the elastic film contracts between the sheet joined portions, the intervals between the sheet joined portions decrease, and pleats are formed to extend in a direction intersecting the stretchable direction between the sheet joined portions in the first sheet layer and the second sheet layer. On the contrary, during stretching, as the elastic film stretches between the sheet joined portions, the intervals between the sheet joined portions and the pleats in the first sheet layer and the second sheet layer widen, and elastic stretching is allowed up to a fully spread state of the first sheet layer and the second sheet layer. It is needless to say that the stretchable region by this elastic film is excellent surface fitting. Further, in the stretchable region, the first sheet layer and the elastic film are not bonded to each other; the second sheet layer and the elastic film are not bonded to each other; and the first sheet layer and the second sheet layer are bonded to each other at very few portions, which leads an advantage that the stretchable region is highly flexible. Additionally, the joint holes of the elastic film advantageously contribute to improvement of air permeability.

Meanwhile, when the stretchable region including such an elastic film is adopted, in order to ensure consistence of texture of an external surface, it is desirable that one sheet of the elastic film is used for forming the largest possible range of the stretchable region. Accordingly, for example, in a disposable wearing article, in a case where an elasticity is imparted to both of a waist portion and an adjacent portion being adjacent to a crotch side of the waist portion, it is preferable that one sheet of the elastic film continues to extend over both the waist portion and the waist adjacent portion being adjacent to the crotch side of the waist portion.

Generally, in a disposable wearing article, a tightening force applied to a waist portion is required to be strong, whereas a tightening force applied to an adjacent portion being adjacent to the waist portion is desirable to be weaker than the tightening force applied to the waist portion.

However, if a region having the same elastic film has a simple structure having only a single layer of the elastic film, a tightening force applied to the region in a direction orthogonal to a stretchable direction cannot be changed significantly.

Accordingly, with such a simple structure, it is difficult to make the tightening force applied to the waist portion sufficiently stronger than the tightening force applied to the adjacent portion being adjacent to the waist portion.

In order to solve this problem, Patent Literature 3 proposes that a stretchable region having an elastic film is folded back at a waist portion to form an integrally duplicate structure, thereby increasing the number of the stacked elastic films. However in this case, there is a concern that air permeability of the waist portion may be lowered.

CITATION LIST

Patent Literature

Patent Literature 1: JP 2016-187387 A
Patent Literature 2: JP 2013-183828 A
Patent Literature 3: JP 2019-118581 A

SUMMARY OF INVENTION

Technical Problem

Therefore, a main object of the invention is to attain an improvement of air permeability of a waist portion of a disposable wearing article in which an elastic film extends over the waist portion and a waist adjacent portion being adjacent to the waist portion, and the waist portion has a dual structure of elastic member.

Solution to Problem

A disposable wearing article that has solved the above problem is as follows.
<First Aspect>
A disposable wearing article including:
a waist portion having an outer side portion exposed on an external surface and an inner side portion overlapped with an inner side of the outer side portion;
a waist adjacent portion continuing to extend from the outer side portion of the waist portion toward a crotch side;
an outer side stretchable region extending over the outer side portion of the waist portion and the adjacent portion being adjacent to the waist portion; and an inner side stretchable region provided in the inner side portion of the waist portion, wherein the outer side stretchable region has
a first sheet layer made of a nonwoven fabric,
a second sheet layer made of a nonwoven fabric, and
an outer side elastic film being interposed therebetween and extending over the outer side portion of the waist portion and the waist adjacent portion, the first sheet layer and the second sheet layer are welded through joint holes penetrating the outer side elastic film at sheet joined portions arranged at intervals, the outer side stretchable region contracts in a width direction by contraction of the outer side elastic film and is extensible in the width direction, the inner side stretchable region includes an inner side elastic member, the inner side stretchable region contracts in the width direction by contraction of the inner side elastic member and is extensible in the width direction, the outer side portion and the inner side portion are joined with each other in a stripe pattern formed by disposing, alternately and repeatedly in the width direction, inner/outer bonded portions continuous in a front-back direction and inner/outer non-bonded portions continuous in the front-back direction, and a natural length in the width direction of the outer side portion is 1.1 to 1.8 times a natural length in the width direction of the inner side portion.

(Effect)

In the present disposable wearing article, firstly, the outer side stretchable region extending over the outer side portion of the waist portion and the waist adjacent portion is stretching and contracting by the same outer side elastic film, so that the waist portion and the adjacent portion being adjacent to the waist portion have consistence of texture of the external surface. Secondary, the present disposable wearing article has not only the outer side elastic film in the outer side portion, but also the inner side elastic member in the inner side portion of the waist portion, which means that the waist portion has a dual structure of elastic member, so that it is easy to make the tightening force applied to the waist portion stronger than the tightening force applied to the adjacent portion being adjacent to the waist portion. Thirdly, the outer side portion and the inner side portion are joined with each other in the stripe pattern, and in addition, the natural length in the width direction of the outer side portion is 1.1 to 1.8 times the natural length in the width direction of the inner side portion, thus, in a worn state (including a natural length state) of being contracted to some extent, in each of the inner/outer non-bonded portions, the outer side portion is lifted from the inner side portion to form a ventilation passage continuous in the front-back direction between the outer side portion and the inner side portion. Therefore, due to the presence of these ventilation passages, air permeability of the waist portion is improved comparing with the article described in Patent Literature 3 in which a waist portion merely has the duplicate structure.

Note that the natural length in the width direction of the outer side portion and the natural length in the width direction of the inner side portion are measured in a state where the outer side portion and the inner side portion are peeled off from each other to separate from each other by means of cutting or the like as necessary.

<Second Aspect>

The disposable wearing article according to the first aspect, further including a folded member extending from the outer side portion, being folded back at an edge of the waist portion, and reaching the inner side portion, wherein vent holes penetrating through the folded member in a thickness direction thereof are formed at intersecting portions of a fold line of the folded member and the inner/outer non-bonded portions, respectively.

(Effect)

The disposable wearing article is preferred to include the folded member described in the present aspect, because in manufacturing, a simple method may be employed in which after the outer side portion and the inner side portion are formed integrally as a member in a state of being flat, this member is folded back at a boundary between the outer side portion and the inner side portion, and then, these side portions are joined with each other. However, in this case, one end of each of the above mentioned ventilation passages formed in the worn state between the outer side portion and the inner side portion is blocked by the folded member. Accordingly, even though the air permeability in the thickness direction of the folded member is remained, the improvement of the air permeability is certainly lowered.

On the contrary, in the present aspect, the above mentioned ventilation passages formed in the worn state between the outer side portion and the inner side portion may communicate with the exterior through the vent holes formed on the edge of the waist portion in the folded member, so that particularly excellent air permeability can be preferably obtained.

<Third Aspect>

The disposable wearing article according to the first or second aspect, further including a folded member extending from the outer side portion, being folded back at an edge of the waist portion, and reaching the inner side portion, wherein the folded member does not include the elastic film extending from the outer side portion, being folded back at the edge of the waist portion, and reaching the inner side portion.

(Effect)

The disposable wearing article is preferred to include the folded member described in the present aspect, because in manufacturing, a simple method may be employed in which after the outer side portion and the inner side portion are formed integrally as a member in a state of being flat, this member is folded back at a boundary between the outer side portion and the inner side portion, and then, these side portions are joined with each other. However, in this case, one end of each of the above mentioned ventilation passages formed in the worn state between the outer side portion and the inner side portion is blocked by the folded member. Accordingly, even though the air permeability in the thickness direction of the folded member is remained, the improvement of the air permeability is certainly lowered, especially when the folded member includes the elastic film.

Therefore, as in the present aspect, it is preferable that the folded member does not include the elastic film extending from the outer side portion, being folded back at the edge of the waist portion, and reaching the inner side portion.

<Fourth Aspect>

The disposable wearing article according to any one of the first to third aspects, wherein the inner side elastic member is formed of a plurality of elongated elastic members continuous in the width direction and arranged at intervals in the front-back direction.

(Effect)

In the present invention, an elastic film may be used as the inner side elastic member, but in that case, the air permeability in the thickness direction of the inner side portion will be inevitably lowered, the improvement of the air permeability by the above mentioned ventilation passages is thereby obstructed as well. Therefore, as in the present aspect, it is preferable that the plurality of elongated elastic members arranged at intervals is provided as the inner side elastic member.

<Fifth Aspect>

The disposable wearing article according to the fourth aspect,
- wherein the inner side portion has the inner side elastic member being adjacent to an internal surface of the outer side portion and a cover layer made of a nonwoven fabric for covering an inner side of the inner side elastic member, and
- the internal surface of the outer side portion and an external surface of the cover layer of the inner side portion are joined with each other in the stripe pattern.

(Effect)

In a case where a stretchable structure having a built-in elastic member is formed, it is common to cover an outer side and an inner side of the elastic member with a sheet made of a nonwoven fabric or the like. Therefore, a pair of sheet layers sandwiching the outer side elastic film may be provided in the outer side portion whereas a pair of sheet layers sandwiching an inner side elastic film as the inner side elastic member may be provided in the inner side portion. However, in such a case, the improvement of the air permeability by the above mentioned ventilation passages is disadvantageously obstructed due to lowering of air permeability particularly in the thickness direction of the inner side portion. On the contrary, as in the present aspect, it is preferable that rubber threads are used as the inner side elastic member, and, these rubber threads are sandwiched between the outer side portion and the cover layer made of the nonwoven fabric, because the air permeability in the thickness direction of the waist portion can be improved.

<Sixth Aspect>

The disposable wearing article according to the first or second aspect,
- further including a folded member extending from the outer side portion, being folded back at an edge of the waist portion, and reaching the inner side portion,
- wherein the folded member has, in a range extending over the outer side portion and the inner side portion, a first nonwoven fabric, a second nonwoven fabric and an elastic film interposed therebetween,
- the first nonwoven fabric and the second nonwoven fabric are welded through joint holes penetrating the elastic film at sheet joined portions arranged at intervals to form a layered body as the folded member,
- a portion of the first nonwoven fabric, a portion of the second nonwoven fabric and a portion of the elastic film, which are located in the outer side portion, form the first sheet layer, the second sheet layer and the outer side elastic film, respectively,
- a portion of the elastic film, which is located in the inner side portion, forms the inner side elastic member,
- the sheet joined portions are not disposed on a fold line of the folded member, and
- intervals in the width direction of sheet joined portions adjacent to an outer side of the fold line of the folded member and intervals in the width direction of sheet joined portions adjacent to an inner side of the fold line of the folded member are narrower than intervals in the width direction of other sheet joined portions.

(Effect)

The disposable wearing article of the present aspect can be preferably manufactured by a simple method in which after not only the outer side portion of the waist portion and the waist adjacent portion, but also the inner side portion of the waist portion are formed integrally as a single layered body in a state of being flat, the layered body is folded back such that the inner side portion is inside the outer side portion, and then, these side portions are joined with each other.

However in such a case, when the sheet joined portions are disposed on the fold line of the folded member, the edge of the waist portion disadvantageously becomes hard in the texture thereof. In addition, since the folded member is likely to bend along an edge of each of the sheet joined portions, it is difficult to stabilize a fold position.

On the contrary, the present aspect is advantageous in that since the sheet joined portions are not disposed on the fold line, the edge of the waist portion does not become hard in the texture thereof, and in addition, the fold position of the folded member can be stabilized.

<Seventh Aspect>

The disposable wearing article according to any one of the first, second and fourth to sixth aspects,
- wherein a maximum elongation in the width direction of the outer side portion is equal to a maximum elongation in the width direction of the inner side portion, and
- an area ratio of the sheet joined portions to the outer side portion in the inner/outer non-bonded portions is larger than an area ratio of the sheet joined portions to the outer side portion in the inner/outer bonded portions.

(Effect)

It is preferable that the maximum elongation in the width direction of the outer side portion is equal to the maximum elongation in the width direction of the inner side portion, because between the outer side portion and the inner side portion, the dimensions in the width direction of components become equal to each other and these components may be produced easily. In this case, by causing the inner side portion to contract more than the outer side portion, a natural length in the width direction of the outer side portion can be made longer than a natural length in the width direction of the inner side portion. Further, the natural length in the width direction of the outer side portion can be adjusted by the area ratio of the sheet joined portions.

Between a case in which an area ratio of the sheet joined portions to the outer side portion in the inner/outer non-bonded portions is larger than that in the inner/outer bonded portions, and a case in which these area ratios are equal to each other, even if a natural length in the width direction of the entire outer side portion is the same, a natural length in the width direction of the outer side portion in the inner/outer non-bonded portions becomes longer in the former case comparing with the latter case. That is, in each of the inner/outer non-bonded portions, the outer side portion is likely to lift more highly from the inner side portion.

<Eighth Aspect>

The disposable wearing article according to any one of the first to seventh aspects,
- wherein the wearing article is an underpants-type disposable wearing article including
  - an integrated outer member from a front body to a back body or outer members separately provided for the front body and the back body, an inner member attached to an intermediate portion of the outer member in a width direction, the inner member extending to both front and back sides of a crotch portion, side seal portions in which both side portions of the outer member in the front body and both side portions of the outer member in the back body are bonded to each other, respectively, and a waist opening and a pair of right and left leg openings, wherein the outer member includes the waist portion and the waist adjacent portion.

(Effect)

The above mentioned stretchable structure of the waist portion is preferably applied to the outer member of the underpants-type disposable diaper as in the present aspect.

Advantageous Effects of Invention

The present invention provides advantages such as an ability to attain an improvement of air permeability of a waist portion of a disposable wearing article in which an elastic film extends over the waist portion and a waist adjacent portion, and the waist portion has a dual structure of elastic member.

BRIEF DESCRIPTION OF DRAWINGS

FIG. 4(a) is a cross-sectional view taken along C-C line of FIG. 1, and FIG. 4(b) is a cross-sectional view taken along E-E line of FIG. 1.

FIG. 20 is a cross-sectional view taken along G-G line of FIG. 1 of a main part of an outer member in a state of being stretched to some extent.

DESCRIPTION OF EMBODIMENTS

Figure 1:
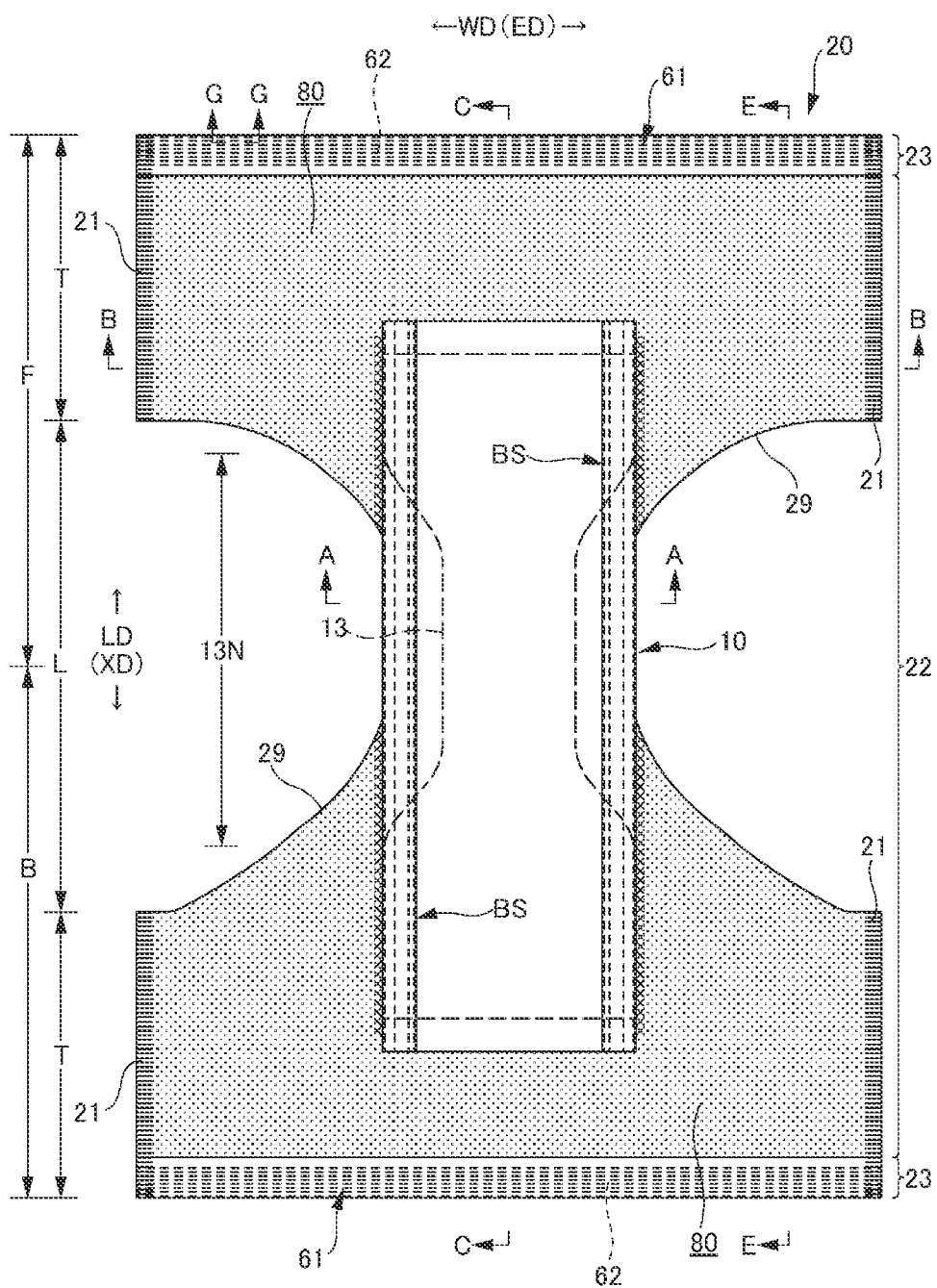
FIG. 1 is a plan view (internal surface side) of an underpants-type disposable diaper in a spread state.

Hereinafter, a detailed description will be given of a disposable wearing article including an elastic film and having a waist portion, based on an example of an underpants-type disposable diaper. In the cross-sectional views, dotted pattern regions represent an adhesive as joining means for joining various components. A hot melt adhesive may be applied using a known technique, such as slot application, bead application in continuous lines or dotted lines, spray application in spiral, Z, or wave shapes, or pattern coating (transfer of a hot melt adhesive by relief printing). In place of or in addition to these, fixing portions of elastic members may be fixed to adjacent members by application of a hot melt adhesive to the outer peripheral surface of the elastic members. Examples of the hot melt adhesive include, but not limited to, EVA-based, pressure-sensitive rubber-based (elastomer-based), polyolefin-based, and polyester/polyamide-based adhesives. The joining means for joining various components may alternatively be material melt-bonding, such as heat sealing or ultrasonic sealing.

FIG. 1 to FIG. 6 illustrate the underpants-type disposable diaper. A reference character LD (longitudinal direction) denotes a front-back direction, and a reference character WD denotes a width direction. The underpants-type disposable diaper (hereinafter also simply referred to as a diaper) includes an outer member 20 forming a front body F and a back body B, and an inner member 10 fixed to and integrated with an inner surface of the outer member 20, and the inner member 10 is formed by interposing an absorbent body 13 between a liquid pervious top sheet 11 and a liquid impervious sheet 12. In manufacturing, after a back surface of the inner member 10 is bonded to the inner surface (upper surface) of the outer member 20 by bonding means such as a hotmelt adhesive, the inner member 10 and the outer member 20 are folded back at a center in the front-back direction LD (longitudinal direction) corresponding to a boundary between the front body F and the back body B, and both side portions thereof are bonded to each other by thermal welding or the hotmelt adhesive to form side seal portions 21, thereby obtaining the underpants-type disposable diaper in which a waist opening and a pair of right and left leg openings are formed.

(Example of Inner Member)

Figure 5:
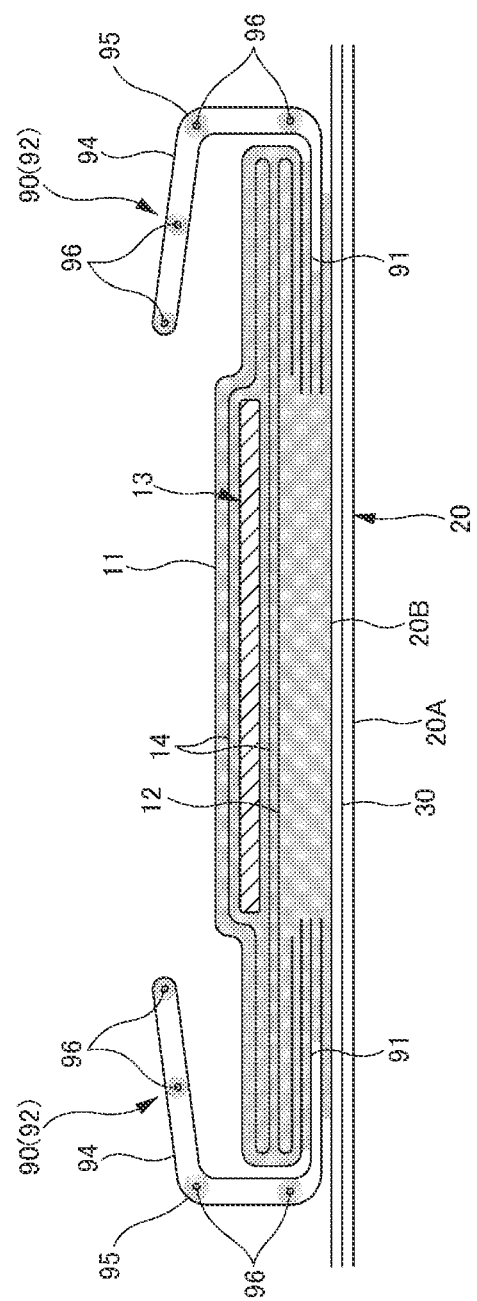
FIG. 5 is a cross-sectional view taken along A-A line of FIG. 1.
Figure 6:
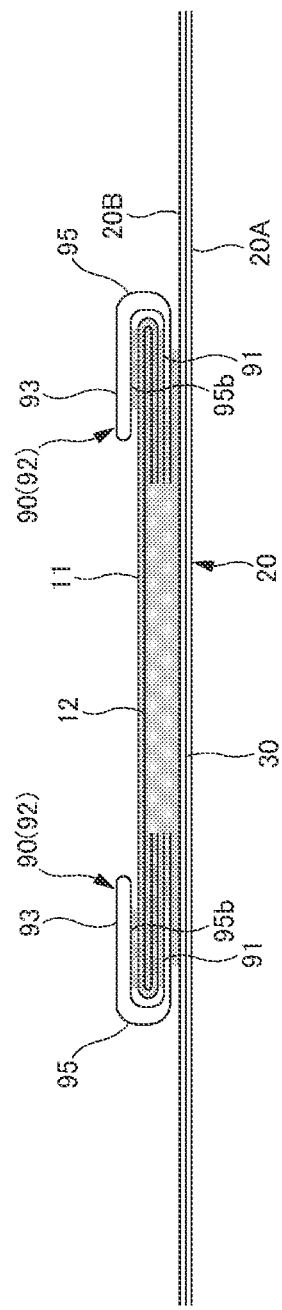
FIG. 6 is a cross-sectional view taken along B-B line of FIG. 1.

As illustrated in FIG. 4 to FIG. 6, the inner member 10 has a structure in which the absorbent body 13 is interposed between the top sheet 11 and the liquid impervious sheet 12 made of polyethylene, etc. and absorbs and holds excretion fluid passing through the top sheet 11. A planar shape of the inner member 10 is not particularly limited. However, a substantially rectangular shape is generally adopted as illustrated in FIG. 1.

As the top sheet 11 that covers the front surface side (skin side) of the absorbent body 13, a perforated or non-perforated nonwoven fabric, a porous plastic sheet, etc. is preferably used. The nonwoven fabric, which is, in the present article, used for the components including the top sheet 11, will be explained in the following. That is, examples of the constituent fibers of the nonwoven fabric include, but not limited to, synthetic fibers, such as polyolefin-based, e.g., polyethylene, polypropylene, or copolymer thereof (copolymer including e.g., polyethylene or ethylene as a component for copolymerization), polyester-based, or polyamide-based fibers (including not only single component fibers, but also composite fibers, such as of core/sheath type), as well as regenerated fibers, such as rayon or cupra, or natural fibers, such as cotton, and also mixtures thereof. For improved flexibility of the nonwoven fabric, the constituent fibers may preferably be crimped fibers. The constituent fibers of the nonwoven fabric may also be hydrophilic fibers (including those rendered hydrophilic with hydrophilizers), hydrophobic fibers, or water-repelling fibers (including those rendered water-repelling with water repellents). Further, the nonwoven fabric may generally be categorized into a discontinuous fiber nonwoven fabric, a continuous fiber nonwoven fabric, a spunbonded nonwoven fabric, a melt blown nonwoven fabric, a spunlace nonwoven fabric, a thermal bonded (air through) nonwoven fabric, a needle-punched nonwoven fabric, a point-bonded nonwoven fabric, a composite nonwoven fabric (SMS or SMMS nonwoven fabric having melt blown layer interposed between spunbonded layers), or the like, generally depending on the length of the fibers, method of forming the sheet, method of joining the fibers, or layered structure, and any of these nonwoven fabrics may be used.

As the liquid impervious sheet 12 covering the back surface side (non-skin contact side) of the absorbent body 13, a liquid impervious plastic sheet such as polyethylene or polypropylene may be used. In particular, a sheet having a moisture penetration property may be preferably used from a viewpoint of preventing stuffiness. Examples thereof include a microporous sheet obtained by melt-kneading an inorganic filler in a polyolefin resin such as polyethylene or polypropylene, molding the melt-kneaded mixture into a sheet, and then stretching the sheet in a uniaxial or biaxial direction.

As the absorbent body 13, it is possible to use a known one, which is based on, for example, a pulp fiber stack, an assembly of filaments of cellulose acetate, etc., or a nonwoven fabric and which has a high-absorbent polymer mixed therewith or fixed thereto, or the like as necessary. To hold the shape and the polymer and for other purposes, the absorbent body 13 can be wrapped in a wrapping sheet 14 having a liquid pervious and liquid retaining property such as crepe paper as necessary.

The absorbent body 13 is formed into a substantially hourglass shape having a narrower portion 13N narrower than both front and back sides at a crotch portion. A size of the narrower portion 13N can be determined as appropriate. A length of the narrower portion 13N in the front-back direction can be set to about 20 to 50% of a maximum length of the diaper, and a width of a narrowest portion thereof can be set to about 40 to 60% of a maximum width of the absorbent body 13. In the case of having such a narrower portion 13N, when the planar shape of the inner member 10 is substantially rectangular, non-absorbent body side portions 17 not having the absorbent body 13 are formed at a portion corresponding to the narrower portion 13N of the absorbent body 13 in the inner member 10.

The liquid impervious sheet 12 is folded back to the back surface side on both sides of the absorbent body 13 in the width direction together with the top sheet 11. As this liquid impervious sheet 12, a microporous sheet may preferably be used which is obtained by kneading a pigment or an inorganic filler such as calcium carbonate, titanium oxide, zinc oxide, white carbon, clay, talc, or barium sulfate in a polyolefin-based resin such as polyethylene or polypropylene, molding the kneaded mixture into a sheet, and then stretching the sheet in a uniaxial or biaxial direction. Alternatively, as the liquid impervious sheet 12, a nonwoven fabric to which improved waterproof property is applied may be used.

Three-dimensional gathers 90 fit around the legs are formed on both side portions of the inner member 10. As illustrated in FIG. 5 and FIG. 6, each of the three-dimensional gathers 90 includes a fixed portion 91 fixed to a side portion of the back surface of the inner member 10, a main unit section 92 extending from the fixed portion 91 up to a side portion of the front surface of the inner member 10 through a side of the inner member 10, a fallen portion 93 formed by front and back end portions of the main unit section 92 fixed to the side portion of the front surface of the inner member 10 (top sheet 11 in the illustrated example) in a fallen state using a hotmelt adhesive 95b, etc., and a free portion 94 formed between parts of the fallen portion 93 which are not fixed. Each of these portions is formed of a gather sheet 95 that is a duplicate sheet obtained by folding a sheet such as a nonwoven fabric. The gather sheet 95 is attached over the entire inner member 10 in the front-back direction, the fallen portion 93 is provided on the front side and the back side of each of the non-absorbent body side portions 17, and the free portion 94 extends to both the front and back sides of the non-absorbent body side portion 17. In addition, between facing surfaces of the duplicate gather sheet 95, gather elastic members 96 are disposed at a tip portion and the like of the free portion. As illustrated in FIG. 5, the gather elastic members 96 are for raising the free portion 94 by an elastic contraction force in a product state.

A fixing structure of the gather elastic members 96 and the gather sheets 95 is not particularly limited. For example, as in the example illustrated in FIG. 5 and FIG. 6, it is possible to adopt a structure described in the following. In portions other than the fallen portion 93, the gather elastic members 96 are attached and fixed to the gather sheets 95 through a hotmelt adhesive at positions of the gather elastic members 96, and facing surfaces of the gather sheets 95 are bonded to each other. However, in the fallen portion 93, the hotmelt adhesive is not present at the positions of the gather elastic members 96. Therefore, the gather elastic members 96 and the gather sheets 95 are not attached to each other, and the facing surfaces of the gather sheets 95 are not bonded to each other at positions having the gather elastic members 96.

As the gather elastic members 96, it is possible to use normally used materials such as polystyrene-based rubber, polyolefin-based rubber, polyurethane-based rubber, polyester-based rubber, polyurethane, polyethylene, polystyrene, styrene-butadiene copolymer, silicone, polyester, etc. In addition, to make it difficult to see from the outside, it is preferable that a fineness is set to 925 dtex or less, a tension is set to 150 to 350%, and an interval is set to 7.0 mm or less for arranging the gather elastic members 96. Incidentally, as the gather elastic members 96, it is possible to use a tape-like member having a certain width in addition to an elongated member as in the illustrated example.

With regard to the gather sheets 95, to prevent passage of urine, etc., prevent a rash, and enhance a feel to a skin (dry feeling), it is preferable to use a water repellent nonwoven fabric coated with a silicone-based, paraffin metal-based, or alkylchromic chloride-based water repellent agent, etc.

As illustrated in FIG. 3 to FIG. 6, the back surface of the inner member 10 is bonded to the inner surface of the outer member 20 by a hotmelt adhesive, etc. in an inner/outer fixing region 10B (shaded region). The inner/outer fixing region 10B may be determined as appropriate and may correspond to almost the entire inner member 10 in a width direction WD. However, it is preferable that both ends in the width direction of the inner/outer fixing region 10B are not fixed to the outer member 20.

(Example of Outer Member)

The outer member 20 includes at least the lower torso portion T of the front body F and the lower torso portion T of the back body B, and further includes an intermediate portion L corresponding to a range in the front-back direction between the lower torso portion T of the front body F and the lower torso portion T of the back body B in the illustrated example. A planar shape of the outer member 20 is formed by narrowing the intermediate portion L so that both side edges 29 of the intermediate portion L in the width direction form leg openings, respectively (the width of the intermediate portion L is smaller than the width of the lower torso portion T). The outer member 20 may be formed separately in the front body F and the back body B, and both bodies may be disposed to be separated in the front-back direction LD of the diaper at the crotch portion.

The lower torso portion T of the outer member 20 refers to a range in the front-back direction of a portion having the side seal portions 21. The lower torso portion T has the waist portion 23 forming an edge portion of the waist opening. The waist portion 23 has an outer side portion 60 exposed on an external surface and an inner side portion 61 overlapped with the inner side of the outer side portion 60. A portion, which continues to extend from the outer side portion 60 of the waist portion 23 of the front body F and from the outer side portion 60 of the waist portion 23 of the back body B toward a crotch side, is an adjacent portion 22 being adjacent to the waist portion 23. Usually, in a case where the lower torso portion T has a boundary in which stretching stress (contraction force during stretching) in the width direction WD changes, a portion closer to the waist opening than the boundary closest to the waist opening is the waist portion 23.

In a case where there is no such a boundary, a portion closer to the waist opening than the absorbent body 13 or the inner member 10 is the waist portion 23. The lengths in the front-back direction LD thereof vary depending on the size of a product and can be appropriately determined. For example, the dimension in the front-back direction LD of the waist portion 23 may be set to 20 to 40 mm. Meanwhile, both side edges of the intermediate portion L are each narrowed in a substantially U shape or a curved shape so as to follow a periphery of a wearer's leg, and these side edges are portions along the peripheries of the wearer's legs. Referring to the outer member 20, as in the illustrated example, in a crotch portion, side edges of the outer member 20 may be located on a central side from side edges of the inner member 10 or located on an outer side thereof in the width direction.

Figure 7:
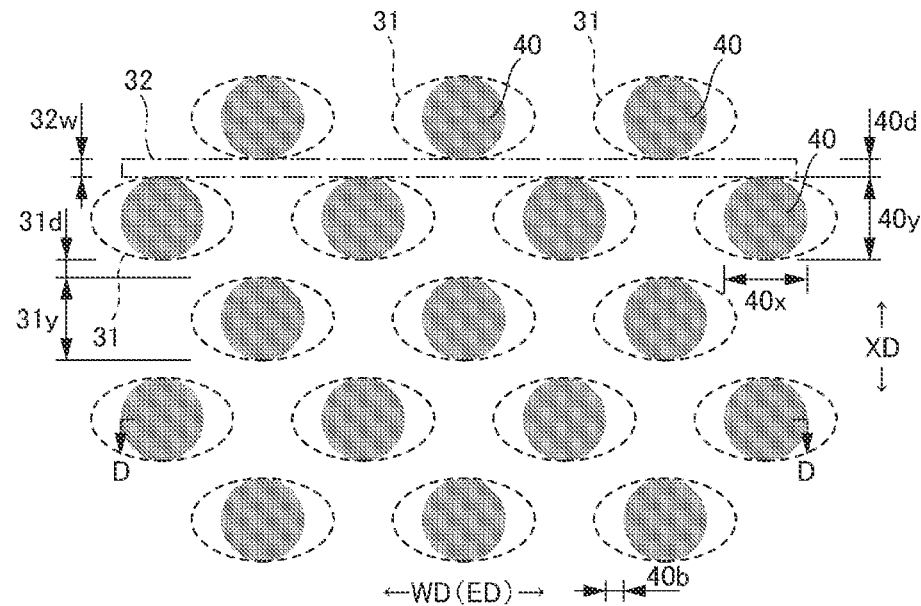
FIG. 7(a) is a plan view of a main part of a stretchable region.
FIG. 7(b) is a cross-sectional view taken along D-D line of FIG. 7(a)
FIG. 7(c) is a cross-sectional view in a worn state.
FIG. 7(d) is a cross-sectional view in a natural length state.
Figure 7:
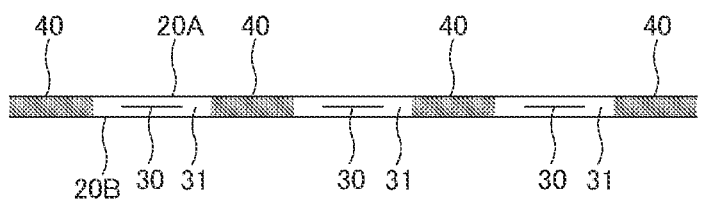
Figure 7:
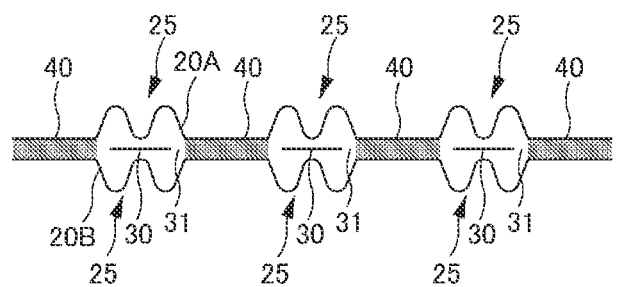
Figure 7:
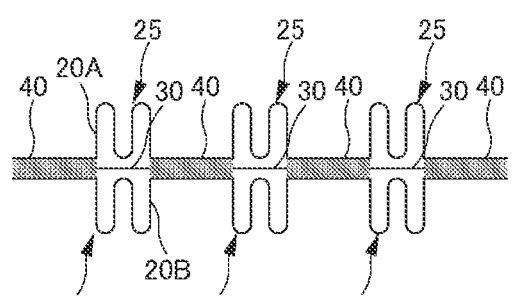
Figure 9:
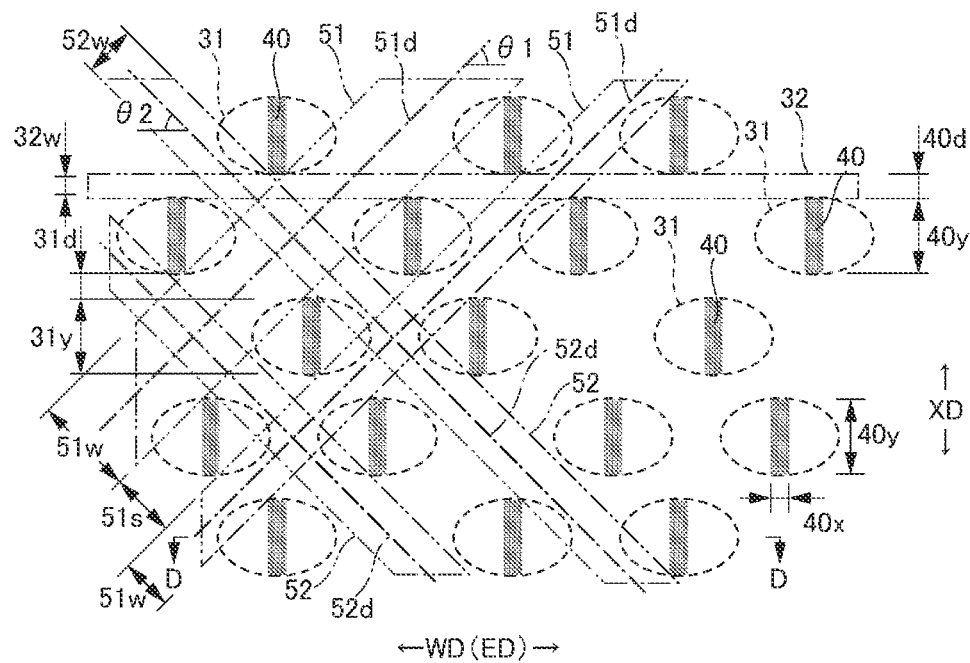
FIG. 9(a) is a plan view of a main part of a stretchable region.
FIG. 9(b) is a cross-sectional view taken along D-D line of FIG. 9(a)
FIG. 9(c) is a cross-sectional view in a worn state.
FIG. 9(d) is a cross-sectional view in a natural length state.
Figure 9:
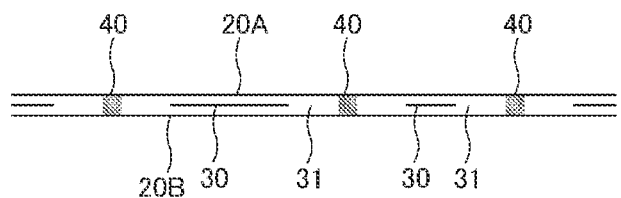
Figure 9:
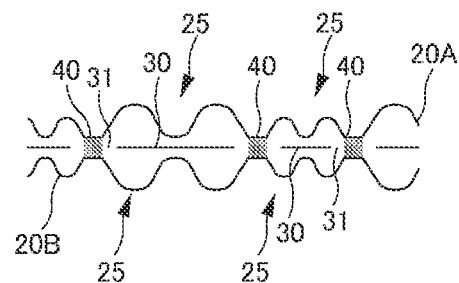
Figure 9:
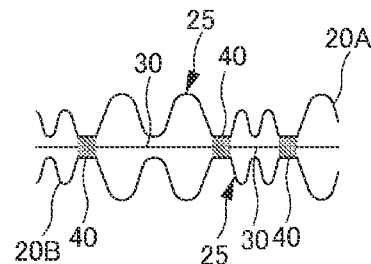

Further, the outer side portion 60 of the waist portion 23 and the adjacent portion 22 being adjacent to the waist portion 23 have, except for middle in the front-back direction LD of the intermediate portion L, the first sheet layer 20A disposed on the outer side, the second sheet layer 20B disposed on the inner side, and an outer side elastic film 30 interposed therebetween, and the outer side elastic film 30 extends over the outer side portion 60 of the waist portion 23 and the adjacent portion 22 being adjacent to the waist portion 23 as illustrated in FIG. 2 and FIG. 4 to FIG. 6. In addition, the first sheet layer 20A and the second sheet layer 20B are bonded through joint holes 31 penetrating the outer side elastic film 30 at a plurality of sheet joined portions 40 arranged at intervals as illustrated in FIG. 7, FIG. 9, etc. That is, the outer member 20 is an elastic member including the outer side elastic film 30. Hereinafter, a structure where the first sheet layer 20A, the second sheet layer 20B, and the elastic film such as the outer side elastic film 30 are stacked is referred to an elastic film stretchable structure 20X.

Among the waist portion 23 of the front body, the waist portion 23 of the back body, and a portion interposed therebetween, as long as the outer side elastic film 30 continues to extend from the waist portion 23 to the adjacent portion 22 being adjacent to the waist portion 23, in this adjacent portion 22, there may be a part in which the outer side elastic film 30 is not provided. For example, the part in which the outer side elastic film 30 is not provided may be only a middle part in the front-back direction LD of the intermediate portion L as in the outer member 20 in the illustrated example, or the part in which the outer side elastic film 30 is not provided may be the entire intermediate portion L. It is needless to say that the outer side elastic member 30 may continue to extend over the entire outer body 20 in the front-back direction LD including the intermediate portion L.

(Bonding Structure of Sheet Joined Portions)

When the first sheet layer 20A and the second sheet layer 20B are bonded at the sheet joined portions 40 through the joint holes 31 formed in the outer side elastic film 30, it is desirable that the first sheet layer 20A and the second sheet layer 20B are not bonded to the outer side elastic film 30 except at least between the first sheet layer 20A and the second sheet layer 20B in the sheet joined portions 40.

When the first sheet layer 20A and the second sheet layer 20B are welded through the joint holes 31 of the outer side elastic film 30 at the sheet joined portions 40, both the first sheet layer 20A and the second sheet layer 20B may be melted and solidified at the sheet joined portions 40, or only one of the first sheet layer 20A and the second sheet layer 20B may be melted and solidified at the sheet joined portions 40. Further, a molten and solidified material of the outer side elastic film 30 may be interposed in the sheet joined portions 40.

Figure 8:
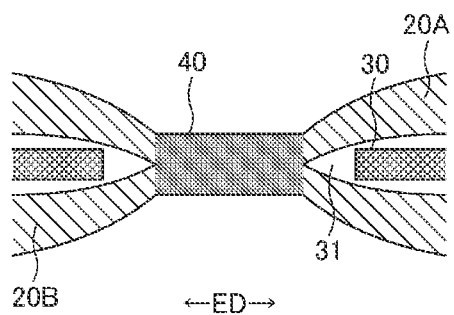
FIGS. 8 (a), 8 (b) and 8 (c) are cross-sectional views schematically illustrating a cross section of a main part of an outer member stretched to some extent.
Figure 8:
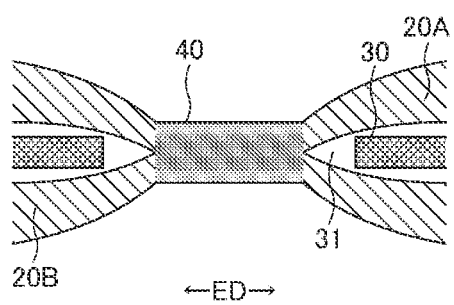
Figure 8:
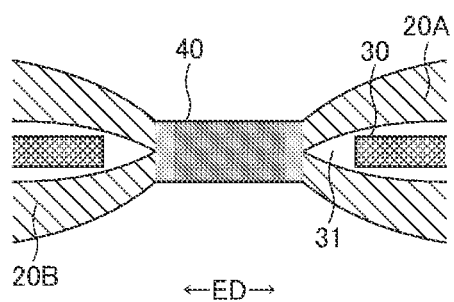

The first sheet layer 20A and the second sheet layer 20B may be uniformly melted and solidified throughout the sheet joined portions 40 in a thickness direction and a planar direction as in the example illustrated in FIG. 8(a) or non-uniformly melted and solidified as indicated by dot pattern gradation in FIGS. 8(b) and 8(c). For example, the first sheet layer 20A and the second sheet layer 20B may have a lower degree of melting toward the outside in the thickness direction of the sheet joined portions 40 as in the example illustrated in FIG. 8(b). This state includes a state in which almost all fibers of the first sheet layer 20A and the second sheet layer 20B are not melted on the surface of the sheet joined portions 40, a state in which molten and solidified materials and unmelted fibers of the first sheet layer 20A and the second sheet layer 20B are mixed on the surface of the sheet joined portions 40, and a state in which fibers of the first sheet layer 20A and the second sheet layer 20B are melted throughout the sheet joined portions 40 in the thickness direction and a degree of melting changes.

With or without a change in the degree of melting in the thickness direction in the sheet joined portions 40, the degree of melting of the first sheet layer 20A and the second sheet layer 20B may be lower toward the peripheral side of the sheet joined portions 40 as in the example illustrated in FIG. 8(c). This state includes a state in which almost all fibers of the first sheet layer 20A and the second sheet layer 20B are not melted at peripheral edges of the sheet joined portions 40 (however, only when the molten and solidified material of the outer side elastic film 30 which will be explained after is interposed as an adhesive), a state in which molten and solidified materials and unmelted fibers of the first sheet layer 20A and the second sheet layer 20B are mixed at the peripheral edges of the sheet joined portions 40, and a state in which fibers of the first sheet layer 20A and the second sheet layer 20B are melted throughout the sheet joined portions 40 in the planar direction and a degree of melting changes.

Incidentally, in these states, the fact that the fibers of the first sheet layer 20A and the second sheet layer 20B are melted includes the fact that cores of the fibers (not only a core in a composite fiber but also a center portion of a single component fiber) are left and surrounding parts thereof (including not only a sheath in the composite fiber but also a part of the single component fiber on the surface layer side) are melted in addition to the fact that all the fibers are melted.

In addition, a state in which the molten and solidified material of the outer side elastic film 30 is left in the sheet joined portions 40 includes a state of being left in a layer shape while being hardly mixed with the first sheet layer 20A or the molten and solidified material thereof and the second sheet layer 20B or the molten and solidified material thereof therebetween, a state of being mixed with melted and solidified one of the first sheet layer 20A and the second sheet layer 20B, and a state of penetrating to some extent between fibers of not melted and solidified one of the first sheet layer 20A and the second sheet layer 20B or between remaining fibers (including cores) in melted and solidified one of the first sheet layer 20A and the second sheet layer 20B.

In the state in which the molten and solidified material of the outer side elastic film 30 is left in the sheet joined portions 40, under the condition that a melting point of at least one of the first sheet layer 20A and the second sheet layer 20B is higher than a melting point of the outer side elastic film 30, the outer side elastic film 30 is interposed between the first sheet layer 20A and the second sheet layer 20B, a site corresponding to the sheet joined portions 40 is pressurized and heated, and at least one of the first sheet layer 20A and the second sheet layer 20B and the outer side elastic film 30 are melted. In this way, manufacturing can be performed.

In this case, the melting point of the outer side elastic film 30 is preferably about 80 to 145° C., the melting points of the first sheet layer 20A and the second sheet layer 20B are preferably about 85 to 190° C., particularly 150 to 190° C., and a difference between the melting point of the first sheet layer 20A and the second sheet layer 20B and the melting point of the outer side elastic film 30 is preferably about 60 to 90° C. In addition, the heating temperature is preferably set to about 100 to 150° C.

Figure 18:
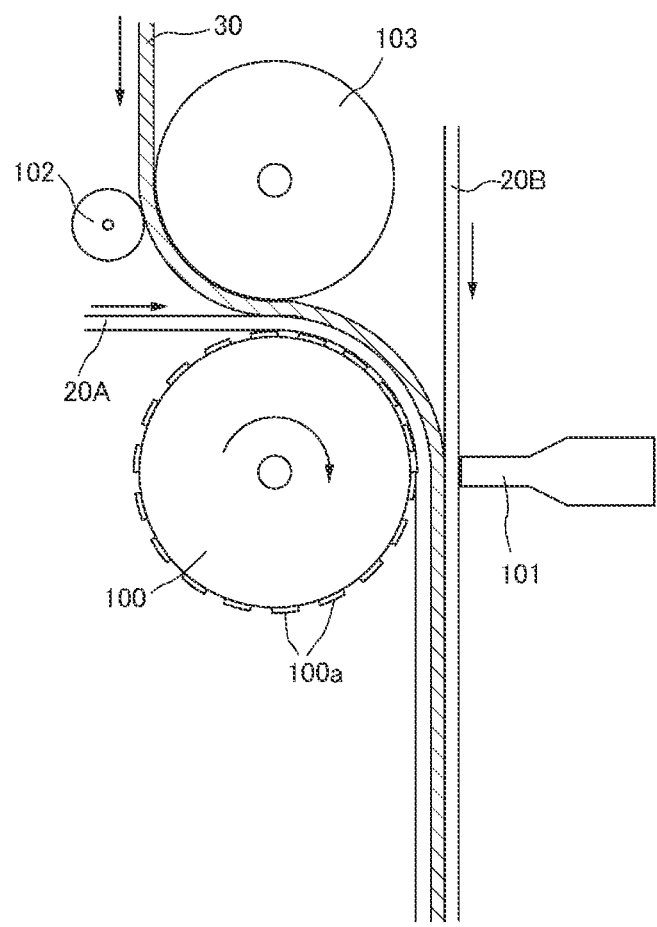
FIG. 18 is a schematic view of an ultrasonic sealing device.

FIG. 18 illustrates an example of a suitable ultrasonic sealing device. In this ultrasonic sealing device, when the sheet joined portions 40 are formed, the first sheet layer 20A, the outer side elastic film 30, and the second sheet layer 20B are fed between an anvil roll 100 having projections 100a formed in the pattern of the sheet joined portions 40 on an outer surface and an ultrasonic horn 101. At this time, for example, by setting a feeding speed of the upstream outer side elastic film 30 by a feed drive roll 103 and a nip roll 102 to be lower than a feeding speed on the anvil roll 100 and the ultrasonic horn 101, the outer side elastic film 30 is stretched to a predetermined stretch rate in an MD (machine direction, flow direction) through a path from a nip position by the feed drive roll 103 and the nip roll 102 to a seal position by the anvil roll 100 and the ultrasonic horn 101. The stretch rate of the outer side elastic film 30 can be set by selecting a speed difference between the anvil roll 100 and the feed drive roll 103, and can be set to about 300% to 500%, for example.

The first sheet layer 20A, the outer side elastic film 30, and the second sheet layer 20B fed between the anvil roll 100 and the ultrasonic horn 101 are heated by ultrasonic vibration energy of the ultrasonic horn 101 while being pressurized between the projections 100a and the ultrasonic horn 101 in a state of being stacked in this order. By melting only the outer side elastic film 30 or melting at least one of the first sheet layer 20A and the second sheet layer 20B and the outer side elastic film 30, the joint holes 31 are formed in the outer side elastic film 30. At the same time, the first sheet layer 20A and the second sheet layer 20B are bonded through the joint holes 31. Therefore, in this case, by selecting a size, a shape, a separation interval, and an arrangement pattern in a roll length direction and a roll circumferential direction of the projections 100a of the anvil roll 100, it is possible to select an area ratio of the sheet joined portions 40.

A reason why the joint holes 31 are formed may not be clear. However, it is considered that the holes are formed when portions corresponding to the projections 100a of the anvil roll 100 in the outer side elastic film 30 are melted and detached from the surroundings while portions corresponding to the projections 100a of the anvil roll 100 in the first sheet layer 20A and the second sheet layer 20B are continued (not detached) from the surroundings. In this instance, a portion between adjacent joint holes 31 aligned in the stretchable direction ED in the outer side elastic film 30 is cut from portions on both sides in the stretchable direction by the joint holes 31 as illustrated in FIGS. 7(a) and 7(b), FIGS. 9(a) and 9(b), FIG. 12, and FIG. 13, and loses support on both sides in a contracting direction. Thus, in a range in which continuity in a direction orthogonal to the contracting direction can be maintained, a center side in the direction LD orthogonal to the stretchable direction ED more contracts until the center side is balanced with a center side in the stretchable direction, and the joint holes 31 enlarge in the stretchable direction ED.

The constituent material of the first sheet layer 20A and the second sheet layer 20B can be used without particular limitation as long as it is a nonwoven fabric in which at least a part of the fibers can be welded (that is, as long as the nonwoven fabric includes a thermoplastic resin component.) Examples thereof may include a polyolefin-based synthetic fiber such as polyethylene or polypropylene, a polyester-based synthetic fiber, a polyamide-based synthetic fiber, etc., a mixed fiber in which two or more of these types are used, or a composite fiber containing two or more of these components (for example, a core-sheath type in which a sheath component is easily melt). Further, the nonwoven fabric may be manufactured by any processing.

Figure 24:
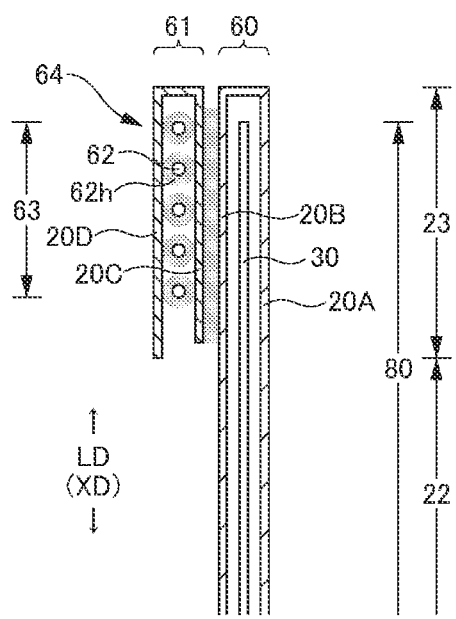
FIGS. 24(a) and 24(b) both are main parts of inner/outer bonded portions.
Figure 24:
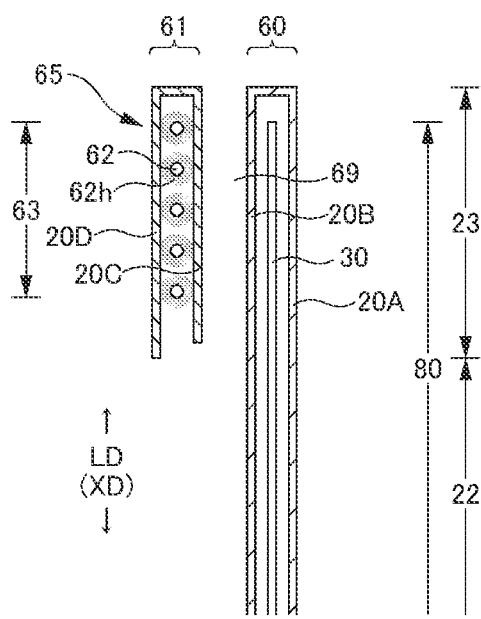

A basis weight of a nonwoven fabric used for the first sheet layer 20A and the second sheet layer 20B is preferably set to about 10 to 25 g/m$^2$. Further, as shown in FIG. 24, a part or all of the first sheet layer 20A and the second sheet layer 20B may correspond to a pair of layers faced to each other by folding a single sheet of a nonwoven fabric. That is, as in the illustrated example, a single sheet of a nonwoven fabric is folded back at an edge of the waist opening such that a portion at one side and a portion at the other side refer to the second sheet layer 20B and the first sheet layer 20A, respectively, with respect to a fold line as a boundary, and the outer side elastic film 30 is interposed between these sheet layers. Naturally, as shown in the other figures, the constituent material of the first sheet layer 20A and the constituent material of the second sheet layer 20B may be individually provided over the entire region in the front-back direction LD.

As the outer side elastic film 30, in addition to a non-porous sheet, it is possible to use a sheet in which a plurality of holes or slits is formed for the air permeability. In particular, it is preferable that the outer side elastic film 30 has a tensile strength in the width direction WD (stretchable direction ED, MD) of 8 to 25 N/35 mm, a tensile strength in the front-back direction LD (direction XD orthogonal to the stretchable direction, CD (cross direction)) of 5 to 20 N/35 mm, a tensile elongation in the width direction WD of 450 to 1,050%, and a tensile elongation in the front-back direction LD of 450 to 1,400%. A thickness of the outer side elastic film 30 is not particularly limited. However, the thickness is preferably about 20 to 40 µm.

(Outer Side Stretchable Region)

In the outer member 20, the outer side portion of the waist portion 23 and the waist adjacent portion 22 have an outer side stretchable region 80 which is contracted in the width direction WD by a contraction force of the outer side elastic film 30 and is extensible in the width direction WD (that is, the stretchable direction ED is the width direction WD of the diaper). More specifically, in a state where the outer side elastic film 30 is stretched in the width direction WD, the first sheet layer 20A and the second sheet layer 20B are bonded through the joint holes 31 of the outer side elastic film 30 at intervals in each of the width direction WD and the orthogonal direction XD orthogonal thereto to form a plurality of sheet joined portions 40, thereby forming the elastic film stretchable structure 20X. Further, in the outer side stretchable region 80, the outer side elastic film 30 is left without disconnection in the width direction WD, and the sheet joined portions 40 are disposed such that the first sheet layer 20A and the second sheet layer 20B contract by the contraction force of the outer side elastic film 30 and contraction pleats 25 are formed, thereby imparting such elasticity. In this way, when the outer side stretchable region 80 extending over the outer side portion 60 of the waist portion 23 and the adjacent portion 22 being adjacent to the waist portion 23 has a structure in which the outer side stretchable region 80 is stretching and contracting by the same outer side elastic film 30, the waist portion 23 and the waist adjacent portion 22 have consistence of texture of the external surface. Further, even in a case where an elongated elastic member such as a rubber thread is used as an inner side elastic member 62 as explained after, the elongated elastic member may be covered by the outer side portion 60 such that it is difficult or it is impossible to recognize visually the elongated elastic member through the external surface.

Figure 11:
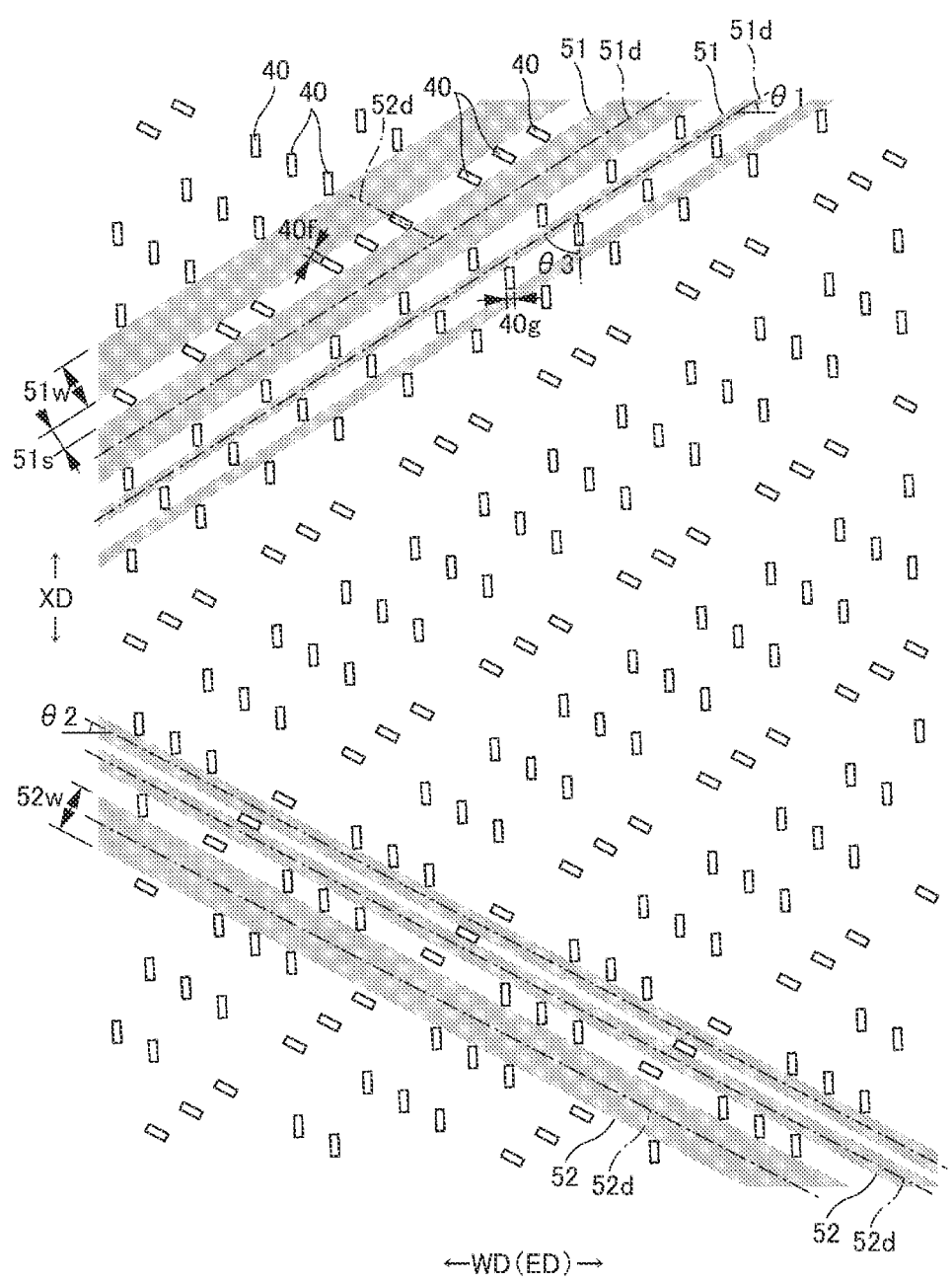
FIG. 11 is a plan view of the stretchable region in the spread state.
Figure 12:
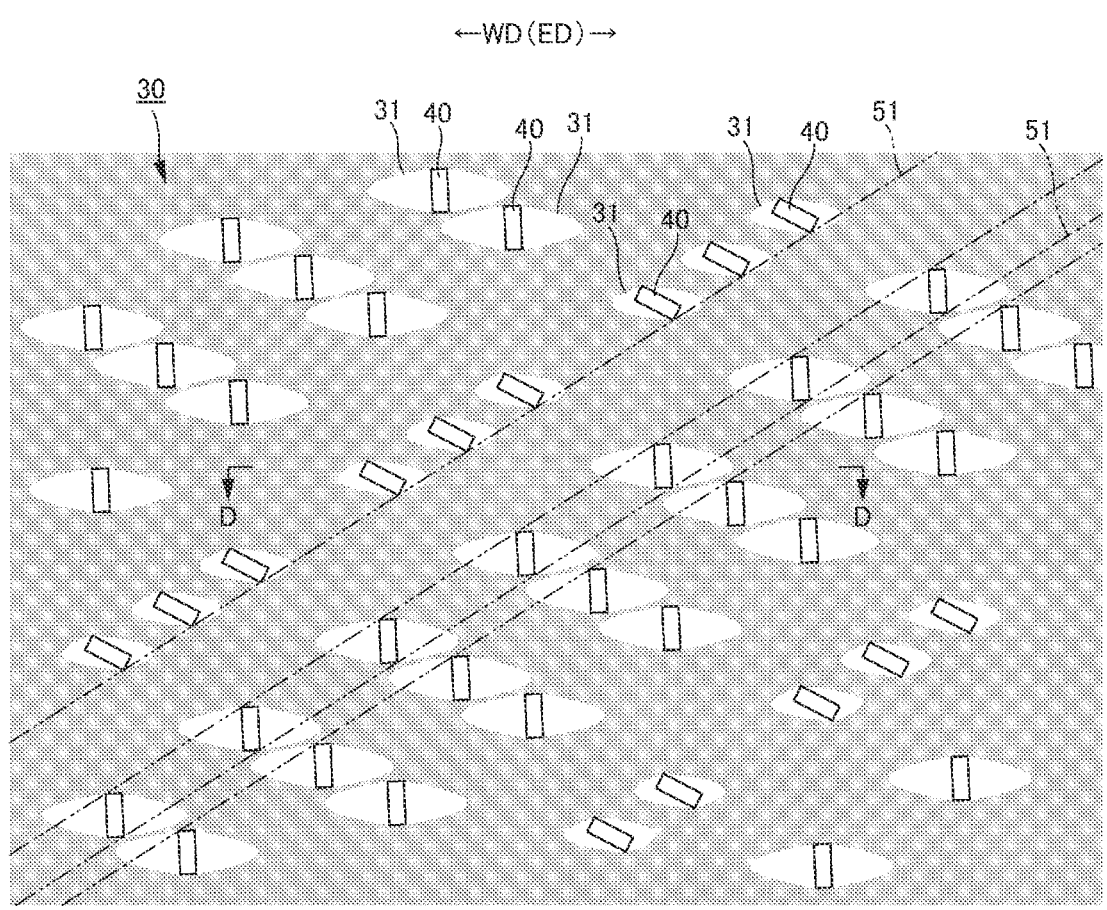
FIG. 12 is an enlarged plan view illustrating a main part of the stretchable region in the spread state.
Figure 13:
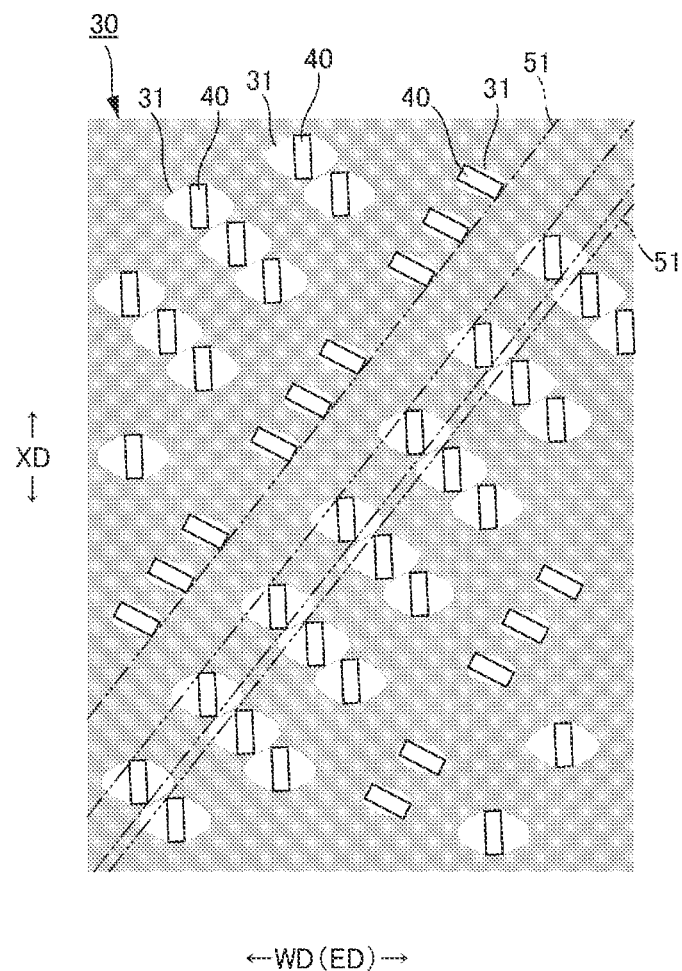
FIG. 13 is an enlarged plan view illustrating a main part of the stretchable region in the natural length state.
Figure 15:
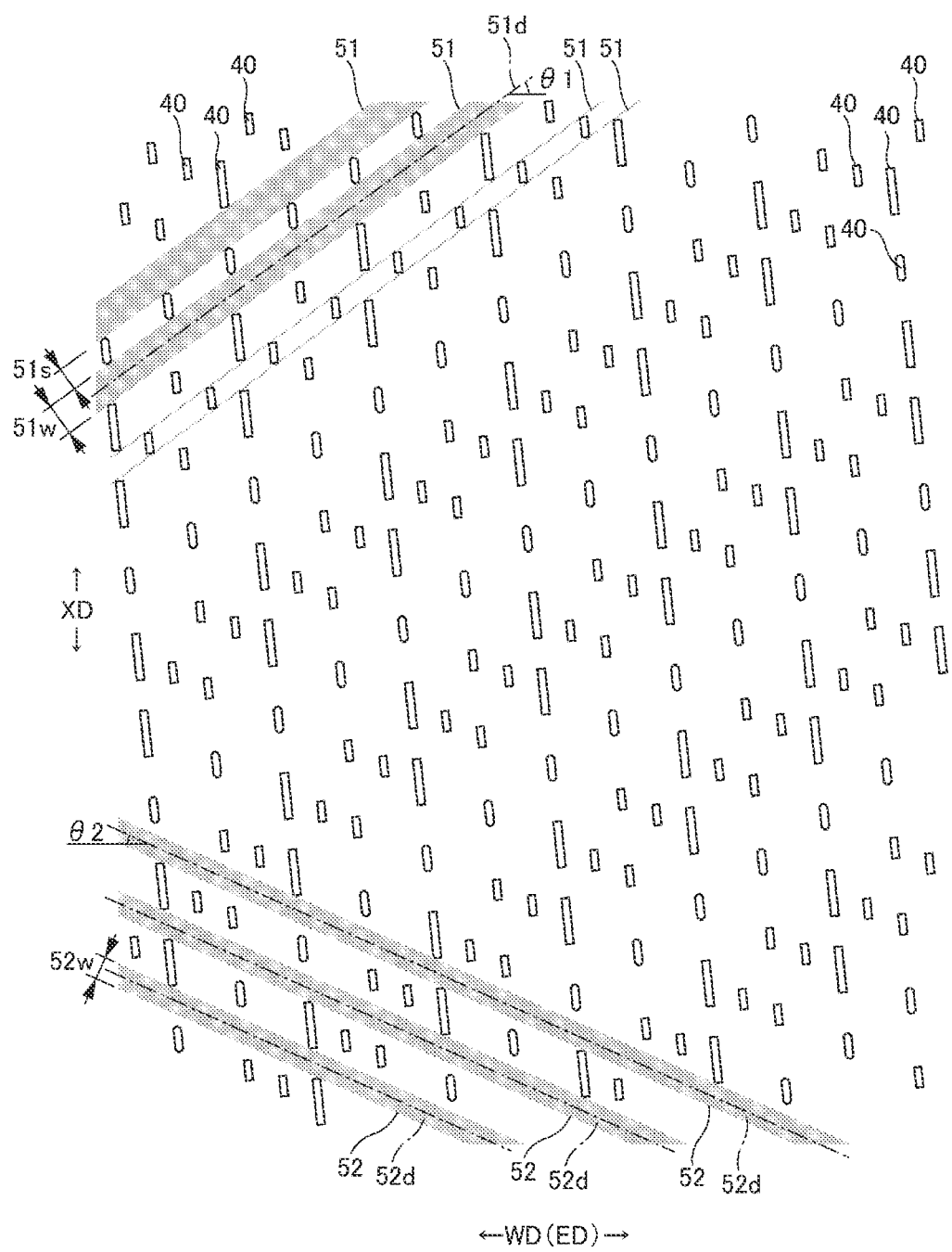
FIG. 15 is a plan view of the stretchable region in the spread state.

In the outer side stretchable region 80 in at least one of the outer side portion 60 of the waist portion 23 and the waist adjacent portion 22, the outer side elastic film 30 may have a hole-less band 32 in which the outer side elastic film 30 is linearly continuous along the width direction WD (that is, the hole-less band 32 is a part having no joint holes 31) as in the examples illustrated in FIG. 7 and FIG. 9 or may not have the hole-less band as in an example illustrated in FIG. 11 and an example illustrated in FIG. 15.

Figure 14:
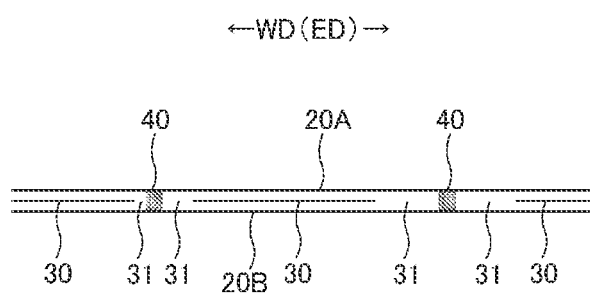
FIG. 14(a) is a cross-sectional view taken along D-D line of FIG. 12.
FIG. 14(b) is a cross-sectional view in the natural length state.
Figure 14:
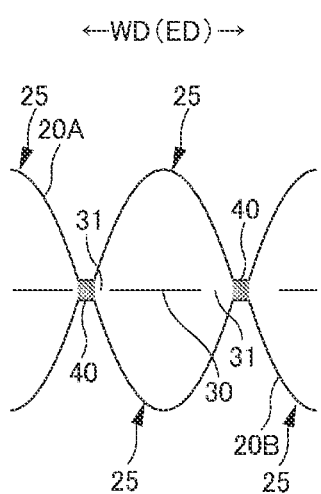

In the outer side stretchable region 80, the first sheet layer 20A and the second sheet layer 20B between the sheet joined portions 40 swell in a direction in which they are separated from each other, thereby forming contraction pleats 25 extending in the orthogonal direction XD in the natural length state as illustrated in FIG. 7(d), FIG. 9(d), and FIG. 14(b). Further, in the worn state of being stretched to some extent in the width direction WD, the contraction pleats 25 are left even though the contraction pleats 25 are extended. In addition, as in the illustrated embodiment, when the first sheet layer 20A and the second sheet layer 20B are not bonded to the outer side elastic film 30 at least in a portion other than between the first sheet layer 20A and the second sheet layer 20B in the sheet joined portions 40, gaps are formed between the sheet joined portions 40 and the joint holes 31 in the outer side elastic film 30, as can be seen from FIG. 7(c) and FIG. 9(c) assuming a worn state and FIGS. 7(a) and 7(b) and FIGS. 9(a) and 9(b) assuming a spread state of the first sheet layer 20A and the second sheet layer 20B, in these states. Even when the material of the outer side elastic film 30 is a non-porous film or sheet, air permeability is imparted by the gaps. In particular, in the case where the outer side elastic film 30 has the hole-less band 32 which is linearly continuous along the width direction WD, the joint holes 31 narrow due to further contraction of the outer side elastic film 30 and a gap is hardly formed between the joint holes 31 and the sheet joined portions 40 in the natural length state. When the outer side elastic film 30 does not have the linearly continuous portion along the width direction WD, gaps remain between the joint holes 31 and the sheet joined portions 40.

It is desirable that a maximum elongation of the outer side stretchable region 80 in the width direction WD is 190% or more (preferably 200 to 220%). The maximum elongation of the outer side stretchable region 80 is substantially determined by the stretch rate of the outer side elastic film 30 at the time of manufacture, and the maximum elongation decreases due to factors that inhibit contraction in the width direction WD based thereon. A main factor of such inhibition is a ratio of the length 40x of the sheet joined portions 40 per unit length in the width direction WD, and the maximum elongation decreases as this ratio increases. In a normal case, since the length 40x of the sheet joined portions 40 has a correlation with an area ratio of the sheet joined portions 40, the maximum elongation of the outer side stretchable region 80 can be adjusted by the area ratio of the sheet joined portions 40.

As in the examples illustrated in FIG. 7 and FIG. 9, in the case where the outer side elastic film 30 has a hole-less band 32 which is linearly continuous along the width direction WD, the stretching stress of the outer side stretchable region 80 can be adjusted mainly by a sum of orthogonal dimensions 32w (equal to intervals 31d of the joint holes) of the hole-less band 32 in which the outer side elastic film 30 is linearly continuous along the width direction WD (see FIG. 7(a) and FIG. 9(a)). On the other hand, as in the example illustrated in FIG. 11 and the example illustrated in FIG. 15, in the case where the outer side elastic film 30 has not the portion which is linearly continuous along the width direction WD, the stretching stress can be adjusted by an intersecting angle between the continuous direction of non-joint bands 51 and 52 and the stretchable direction ED. In a normal case, it is preferable that each of the acute intersecting angles 61 and 62 between the continuous direction of the non-joint bands 51 and 52 and the stretchable direction ED in the spread state is set to be more than 0 degrees and 45 degrees or less, particularly a range of 10 to 30 degrees.

The area ratio of the sheet joined portions 40 and the area of each of the sheet joined portions 40 in the outer side stretchable region 80 can be determined as appropriate and are preferably within the following ranges in a normal case.

Area of each of sheet joined portions 40: 0.14 to 3.5 mm$^2$ (particularly 0.14 to 1.0 mm$^2$)

Area ratio of sheet joined portions 40: 1.8 to 19.1% (particularly 1.8 to 10.6%)

Figure 2:
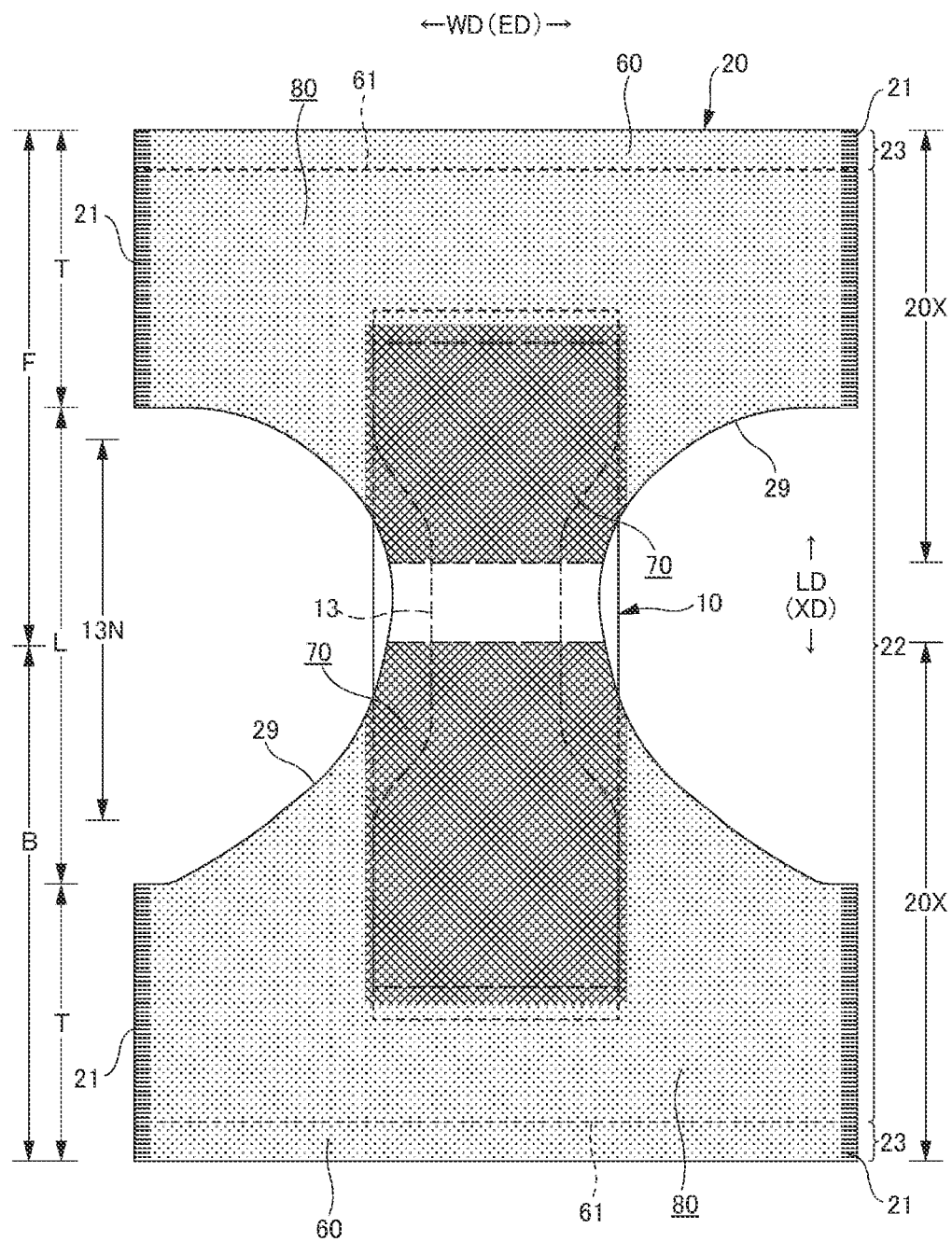
FIG. 2 is a plan view (external surface side) of the underpants-type disposable diaper in the spread state.
Figure 3:
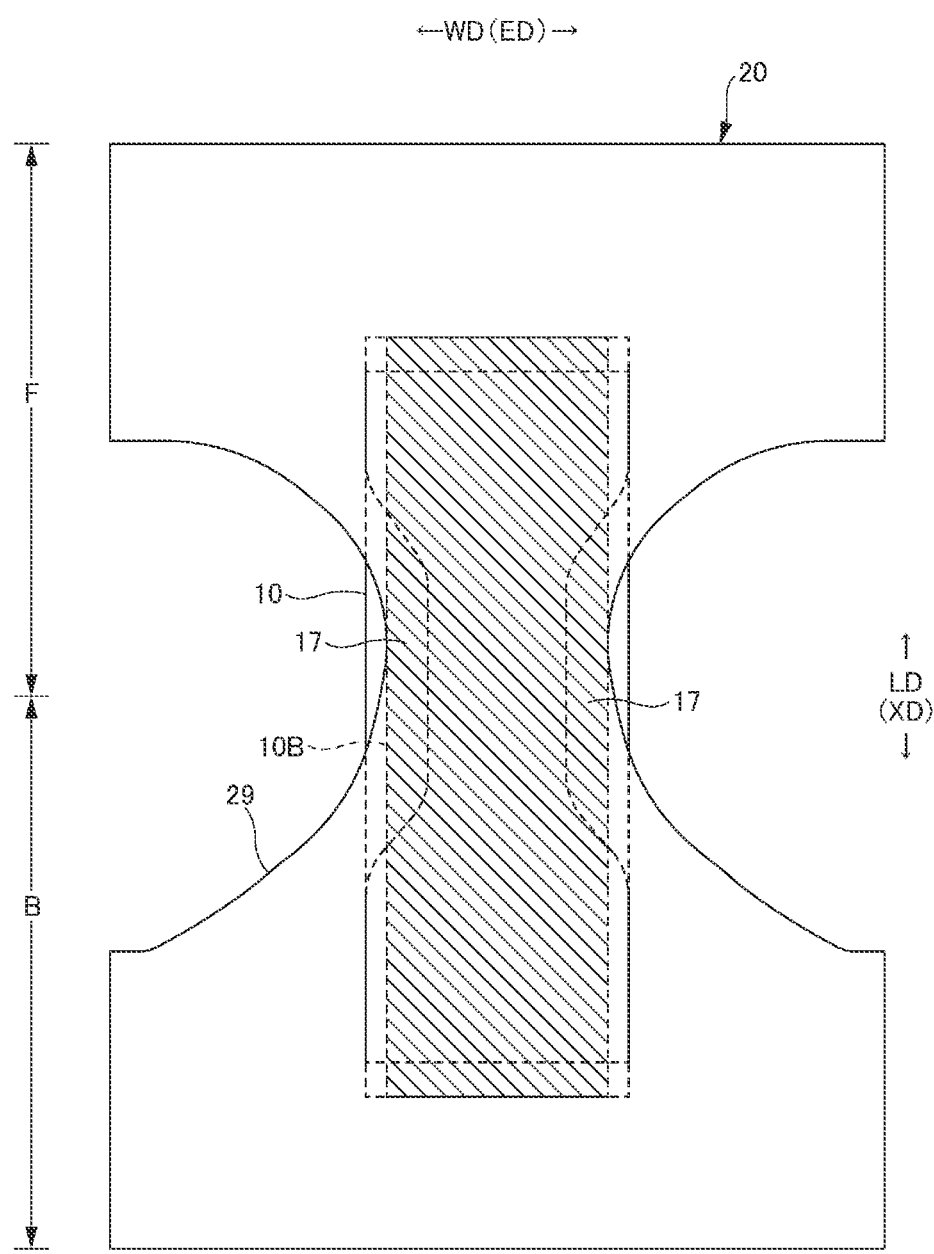
FIG. 3 is a plan view illustrating only a main part of the underpants-type disposable diaper in the spread state.

As described above, the maximum elongation and stretching stress of the outer side stretchable region 80 can be adjusted by the area of the sheet joined portions 40. Thus, as illustrated in FIG. 1 and FIG. 2, a plurality of regions having different area ratios of the sheet joined portions 40 may be provided in the outer side stretchable region 80 to change fitting according to the site.

A shape of each of the sheet joined portions 40 and the joint holes 31 in the natural length state can be determined as appropriate, and may be set to any shape such as a perfect circle, an ellipse, a polygon such as a triangle, a rectangle, or a rhombus, a convex lens shape, a concave lens shape, a star shape, a cloud shape, etc. The dimensions of the individual sheet joined portions are not particularly limited. However, a maximum length 40y (approximately equal to a dimension 31y of the joint holes 31 in the orthogonal direction) is preferably 0.5 to 3.0 mm, particularly preferably 0.7 to 1.1 mm, and a maximum width 40x is preferably 0.1 to 3.0 mm, particularly 0.1 to 1.1 mm in the case of a shape that is long in a direction XD orthogonal to the stretchable direction.

A size of each of the sheet joined portions 40 may be determined as appropriate. When the size is excessively large, an influence of hardness of the sheet joined portions 40 on the texture increases. When the size is excessively small, a bonding area is small, and materials may not sufficiently adhere to each other. Thus, in a normal case, the area of each of the sheet joined portions 40 is preferably set to about 0.14 to 3.5 mm$^2$. It is sufficient that the area of an opening of each of the joint holes 31 is greater than or equal to the area of each of the sheet joined portions since the sheet joined portions are formed through the joint holes 31. However, the area is preferably about 1 to 1.5 times the area of each of the sheet joined portions. Incidentally, the area of the opening of each of the joint holes 31 refers to a value in a state of being integrated with the first sheet layer 20A and the second sheet layer 20B, not in a state of the outer side elastic film 30 alone, and in the natural length state, and refers to a minimum value when the area of the opening of each of the joint holes 31 is not uniform in the thickness direction, for example, the area is different between the front surface and the back surface of the outer side elastic film 30.

Figure 10:
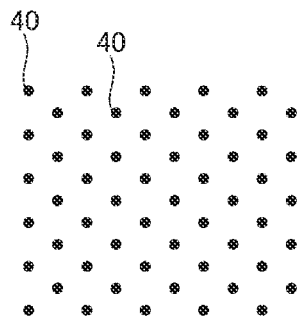
FIGS. 10 (a)-10 (e) are a plan views illustrating various arrangements of sheet joined portions.
Figure 10:
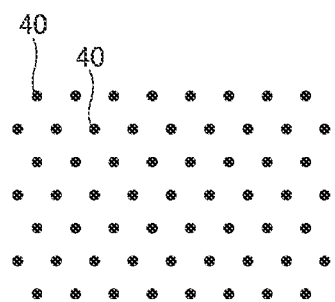
Figure 10:
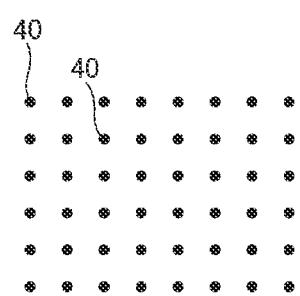
Figure 10:
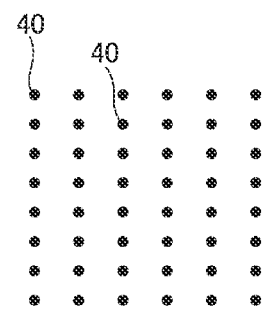
Figure 10:
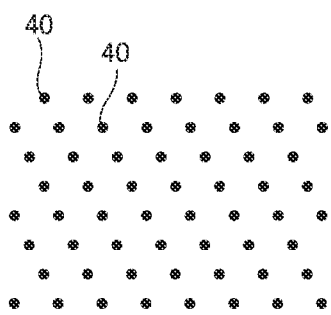

A planar arrangement of the sheet joined portions 40 and the joint holes 31 in the outer side stretchable region 80 can be determined as appropriate. However, a regularly repeated planar arrangement is preferable. In addition to a regularly repeated planar arrangement such as an oblique lattice shape illustrated in FIG. 10(a), a hexagonal lattice shape illustrated in FIG. 10(b) (these shapes are also referred to as staggered shapes), a square lattice shape illustrated in FIG. 10(c), a rectangular lattice shape illustrated in FIG. 10(d), or a parallel lattice shape illustrated in FIG. 10(e) (a form in which two groups of a plurality of parallel rows in an oblique direction are provided to intersect each other as illustrated in the figure) (including shapes obtained by inclining these shapes at an angle less than 90 degrees with respect to the stretchable direction), it is possible to adopt an arrangement in which a group of the sheet joined portions 40 (arrangement in a group unit may be regular or irregular and may correspond to a pattern, a character shape, etc.) is regularly repeated.

An arrangement pattern of the sheet joined portions 40 in the outer side stretchable region 80 is preferably as in the example illustrated in FIG. 9, as in the example illustrated in FIG. 11, and as in the example illustrated in FIG. 15. That is, in these examples, in the outer side stretchable region 80, as non-joint bands 51 and 52 in which a part not having the sheet joined portions 40 is continuous in the spread state, a first non-joint band 51 linearly continuous along a first direction 51d intersecting the stretchable direction ED at an acute angle (acute intersecting angle θ1) is repeatedly present at intervals in a direction orthogonal to the first direction 51d. In addition, a plurality of sheet joined portions 40 and joint holes 31 are provided at intervals between adjacent first non-joint bands 51 in the outer side stretchable region 80. Further, characteristically, a unit structure including a plurality of first non-joint bands 51 having different first widths 51w determined as widths in the direction orthogonal to the first direction 51d is repeatedly present in the direction orthogonal to the first direction 51d in the outer side stretchable region 80.

Figure 17:
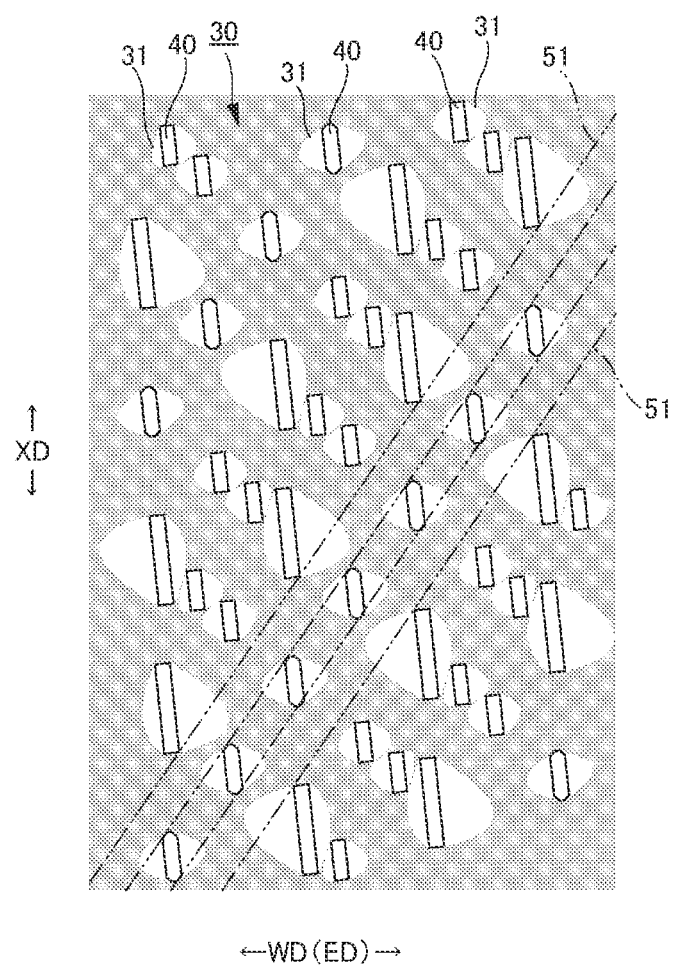
FIG. 17 is an enlarged plan view illustrating the main part of the stretchable region in the natural length state.

As described above, when the unit structure including the plurality of first non-joint bands 51 having different first widths 51w is repeatedly present in the direction orthogonal to the first direction 51d in the outer side stretchable region 80, a similar magnitude change in width is formed in a continuous portion of the outer side elastic film 30 inside the first non-joint bands 51. That is, when the width 51w of the first non-joint bands 51 is narrow, the width of the continuous portion of the outer side elastic film 30 on the inside is narrowed. Further, when the width 51w of the first non-joint bands 51 is wide, the width of the continuous portion of the outer side elastic film 30 on the inside is widened. Further, when there is a change in the first width 51w in the continuous portion of the outer side elastic film 30 in the first non-joint bands 51, both the continuous portion of the outer side elastic film 30 in first non-joint bands 51 having a wide width and the continuous portion of the outer side elastic film 30 in first non-joint bands 51 having a narrow width are visually emphasized. As a result, regardless of whether the outer side stretchable region 80 is in the natural length state (see FIG. 13 and FIG. 17) or in the worn state stretched to some extent, an appearance having beautiful oblique stripe patterns is exhibited. In addition, in a state of being contracted to some extent, a size of the contraction pleats 25 in the first non-joint bands 51 changes according to the first width 51w of the first non-joint bands 51, and thus an oblique stripe pattern appears more clearly due to an influence of the contraction pleats 25.

The unit structure described above is not limited by the magnitude of the width 51w as long as the plurality of first non-joint bands 51 having different first widths 51w is included. However, it is preferable that a large first width 51w in the first non-joint bands 51 is 1.2 to 60 times that of a first non-joint band 51 having a closest width 51w and a small first width 51w is 0.01 to 0.8 times that of the first non-joint band 51 having the closest width 51w.

In addition, in the unit structure described above, as long as the plurality of first non-joint bands 51 having the different first widths 51w is included, the first widths 51w in all the first non-joint bands 51 may be different from each other, and a first width 51w in some of the plurality of non-joint bands 51 may be different from a first width 51w of one or a plurality of other first non-joint bands 51 as illustrated in the figure.

Even if an oblique stripe pattern along the first direction 51d due to the contraction pleats 25 of the first non-joint bands 51 and the continuous portion of the outer side elastic film 30 therein appears in the outer side stretchable region 80, when an oblique stripe pattern along another oblique direction is more strongly visually recognized in the same outer side stretchable region 80, there is concern that the oblique stripe pattern due to the contraction pleats 25 of the first non-joint bands 51 and the continuous portion of the outer side elastic film 30 therein becomes inconspicuous. On the other hand, it is preferable that a maximum value of the first widths 51w in the first non-joint bands 51 is a maximum value of widths in a direction orthogonal to a continuous direction in all the non-joint bands 51, 52 having same or different inclination directions since an oblique stripe pattern due to the contraction pleats 25 of the first non-joint bands 51 and the continuous portion of the outer side elastic film 30 therein is more strongly visually recognized in the outer side stretchable region 80. In this case, the maximum value of the first widths 51w in the first non-joint bands 51 can be determined as appropriate, and is preferably 0.01 to 9 times that of the first non-joint band 51 having the closest width 51w. Incidentally, widths of all the non-joint bands 51 and 52 including the first non-joint bands 51 in the direction orthogonal to the continuous direction are not limited and are preferably within a range of 0.3 to 50 mm in a normal case. Naturally, with regard to the widths of the non-joint bands 51 and 52, for example, the widths of the non-joint bands 51 in the direction orthogonal to the continuous direction thereof correspond to the first widths 51w, and each of these widths has a constant value, because these non-joint bands 51 and 52 are linearly continuous portions.

A first interval 51s determined as an interval between the adjacent first non-joint bands 51 in the direction orthogonal to the first direction 51d can be determined as appropriate. Therefore, the first interval 51s may be the same as, wider than, or narrower than the first width 51w of the adjacent first non-joint bands 51. As one preferable example, it is possible to mention a mode in which the maximum value of the first widths 51w of the first non-joint bands 51 is smaller than a maximum value of the first interval 51s in the unit structure. In this way, by forming a wide interval portion in the unit structure, the oblique stripe pattern due to the contraction pleats 25 of the first non-joint bands 51 and the continuous portion of the outer side elastic film 30 inside thereof is more strongly visually recognized. In this case, the maximum value of the first widths 51w of the first non-joint bands 51 can be determined as appropriate, and is preferably 0.01 to 9 times the maximum value of the first interval 51s. Incidentally, intervals between all the non-joint bands 51 and 52 including the first non-joint bands 51 in the direction orthogonal to the continuous direction are not particularly limited and are preferably within a range of 0.3 to 50 mm in a normal case. Naturally, with regard to the intervals between the adjacent non-joint bands 51 and between the adjacent non-joint bands 52, for example, the intervals between the adjacent non-joint bands 51 in the direction orthogonal to the continuous direction thereof correspond to the first intervals 51s, and each of these intervals has a constant value along the continuous direction.

As non-joint bands 51 and 52, the second non-joint bands 52 linearly continuous along a second direction 52d intersecting the stretchable direction ED at an acute angle (acute intersecting angle 62) other than the first direction 51d may be repeatedly present at intervals in a direction orthogonal to the second direction 52d, or the second non-joint bands 52 may not be present. In one preferable mode having the second non-joint bands 52, the non-joint bands 51 and 52 are formed in an oblique lattice shape in the outer side stretchable region 80, the first non-joint bands 51 are continuous portions in one direction in the non-joint bands 51 and 52 having the oblique lattice shape, and the second non-joint bands 52 are continuous portions in another direction in the non-joint bands 51 and 52 having the oblique lattice shape. In this case, the first direction 51d and the second direction 52d are opposite to each other in terms of inclination with respect to the stretchable direction ED. Incidentally, as in the example illustrated in FIG. 11 and the example illustrated in FIG. 15, even in a mode not having the non-joint bands continuous in the width direction WD (stretchable direction ED), when each of the acute intersecting angles 61 and 62 between the first and second directions 51d and 52d and the stretchable direction ED is 5 to 45 degrees, particularly 10 to 30 degrees in the spread state of the outer side stretchable region 80, elasticity in the outer side stretchable region 80 can be sufficiently ensured.

However, when an oblique stripe pattern along an oblique direction of the second non-joint bands 52 is more strongly visually recognized in the same outer side stretchable region 80, there is concern that the oblique stripe pattern due to the contraction pleats 25 of the first non-joint bands 51 and the continuous portion of the outer side elastic film 30 therein becomes inconspicuous. Therefore, in the case where the second non-joint bands 52 are present as in the example illustrated in FIG. 15, it is desirable that all the second widths 52w determined as a width in the direction orthogonal to the second direction in the second non-joint bands 52 are the same, or the sheet joined portions 40 are disposed so that the second non-joint bands 52 are not present. In this way, in the outer side stretchable region 80, the oblique stripe pattern due to the contraction pleats 25 of the first non-joint bands 51 and the continuous portion of the outer side elastic film 30 inside thereof is more strongly visually recognized.

Figure 16:
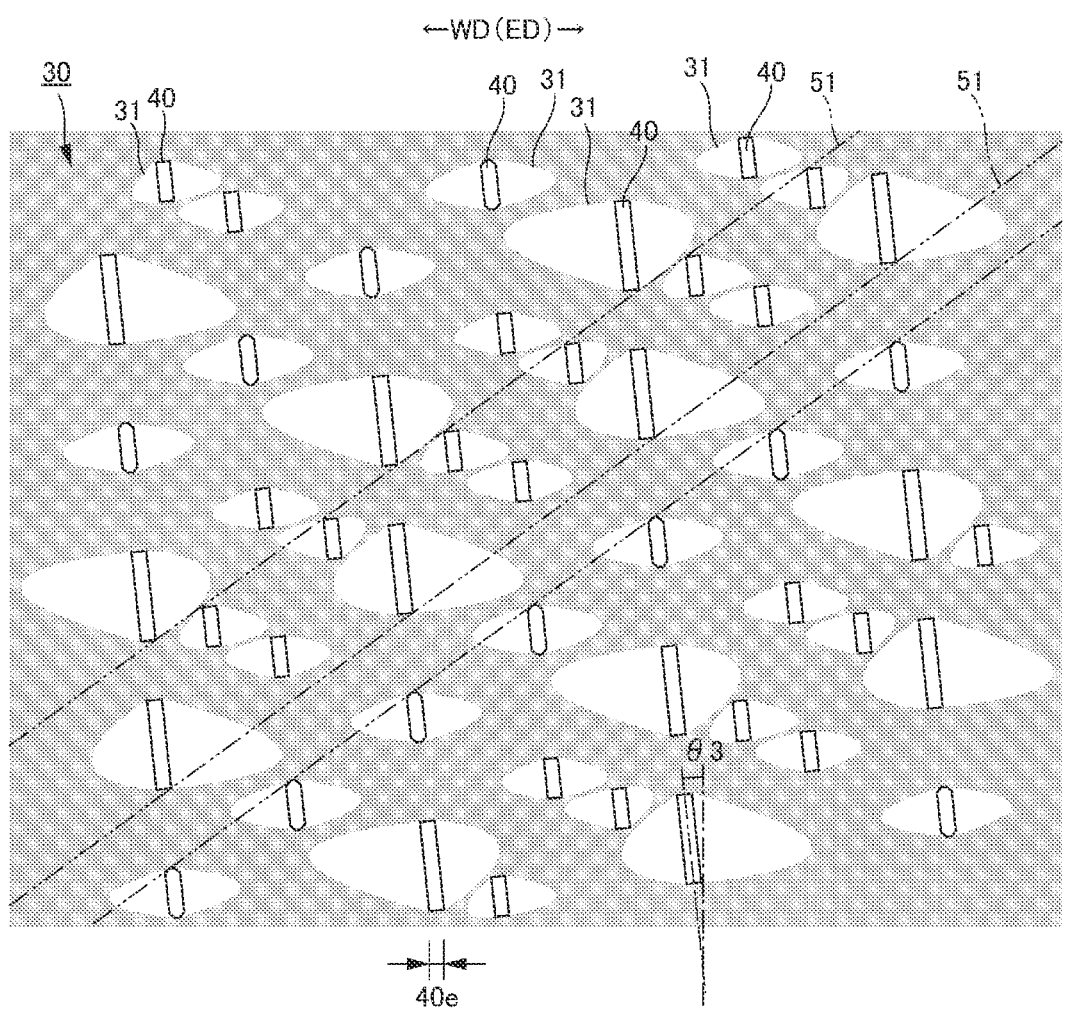
FIG. 16 is an enlarged plan view illustrating the main part of the stretchable region in the spread state.

Meanwhile, between adjacent first non-joint bands 51, the sheet joined portions 40 are aligned in the first direction 51d. In this case, for example, as illustrated in FIG. 16, it is preferable that all the sheet joined portions 40 have an elongated shape in which an acute intersecting angle 63 between the longitudinal direction and the direction orthogonal to the stretchable direction ED is within 10 degrees and a maximum dimension 40e in the stretchable direction ED is 0.1 to 0.4 mm since it is possible to ensure a larger dimension of the first non-joint bands 51 in the stretchable direction ED and to suppress a decrease in elasticity.

In addition, as in the example illustrated in FIG. 11, when the unit structure includes a plurality of first wide non-joint bands 51 having a maximum first width 51w and a plurality of first narrow non-joint bands 51 having a narrower first width 51w adjacent to each other in the direction orthogonal to the first direction 51d, it is preferable that sheet joined portions 40 having an elongated shape in which the acute intersecting angle between the longitudinal direction and the second direction 52d is within 5 degrees and a maximum dimension 40f in the direction orthogonal to the longitudinal direction is 0.1 to 0.4 mm are aligned at intervals in the first direction 51d between the adjacent first wide non-joint bands 51. In addition, it is preferable that sheet joined portions 40 having an elongated shape in which the acute intersecting angle 63 between the longitudinal direction and the first direction 51d is 45 degrees or more and a maximum dimension 40g in the direction orthogonal to the longitudinal direction is 0.1 to 0.4 mm are aligned at intervals in the first direction 51d between the adjacent first narrow non-joint bands 51. By such a shape and arrangement of the sheet joined portions 40, the contraction pleats 25 of the first non-joint bands 51 and the continuous portion of the outer side elastic film 30 therein are particularly visually emphasized due to the small area of sheet joined portions 40.

One row or a plurality of rows of the sheet joined portions 40 (rows of the non-joint bands 51 and 52 in the continuous direction) may be located between the adjacent non-joint bands 51 and 52. In addition, it is preferable that intervals between the sheet joined portions 40 in a row direction are regular. However, all the intervals may not be constant, and some intervals may be different.

(Non-Stretchable Region)

As illustrated in FIG. 2, a non-stretchable region 70 may be provided in the outer side stretchable region 80. The non-stretchable region 70 means that a maximum elongation in the stretchable direction is 120% or less. The maximum elongation of the non-stretchable region 70 is preferably 110% or less, and more preferably 100%. Arrangement of the outer side stretchable region 80 and the non-stretchable region 70 can be determined as appropriate. In the case of the outer member 20 of the underpants-type disposable diaper, a portion overlapping the absorbent body 13 is a region not requiring stretching and contraction. Thus, as in the illustrated embodiment, it is preferable to form a part or all of the portion overlapping the absorbent body 13 in the adjacent portion being adjacent to the waist portion (it is desirable to include almost the entire inner/outer fixing region 10B) into the non-stretchable region 70 while the non-stretchable region is not provided in the outer side stretchable region 80 of the waist portion. That is, the outer side stretchable region 80 of the waist portion 23 continues to extend over the entire waist portion 23 in the width direction WD (excluding the side seal portions 21), and the non-stretchable region 70 is provided in a part of the adjacent portion 22 being adjacent to the waist portion. Naturally, the non-stretchable region 70 may be provided only in a region not overlapping the absorbent body 13.

The shape of each of the sheet joined portions 40 in the non-stretchable region 70 is not particularly limited, and may be appropriately selected from the same shapes as those described before.

In addition, the area ratio of the sheet joined portions 40 and the area of each of the sheet joined portions 40 in the non-stretchable region 70 can be determined as appropriate. However, in a normal case, the area ratio and the area are preferably within the following ranges since the non-stretchable region 70 does not become hard due to the small area of each of the sheet joined portions 40 and the low area ratio of the sheet joined portions 40.

Area of each of sheet joined portions 40: 0.10 to 0.75 mm$^2$ (particularly 0.10 to 0.35 mm$^2$)

Area ratio of sheet joined portions 40: 4 to 13% (particularly 5 to 10%)

The non-stretchable region 70 can be formed by densely disposing the sheet joined portions 40 so that the first sheet layer 20A and the second sheet layer 20B are prevented from being contracted by the contraction force of the outer side elastic film 30 to form pleats. Specific examples of a method for forming the non-stretchable region 70 include those shown in, for example, JP 5980355 B2, JP 5918877 B2, JP 5980367 B2, and JP 6049228 B2.

(Inner Side Portion)

Figure 19:
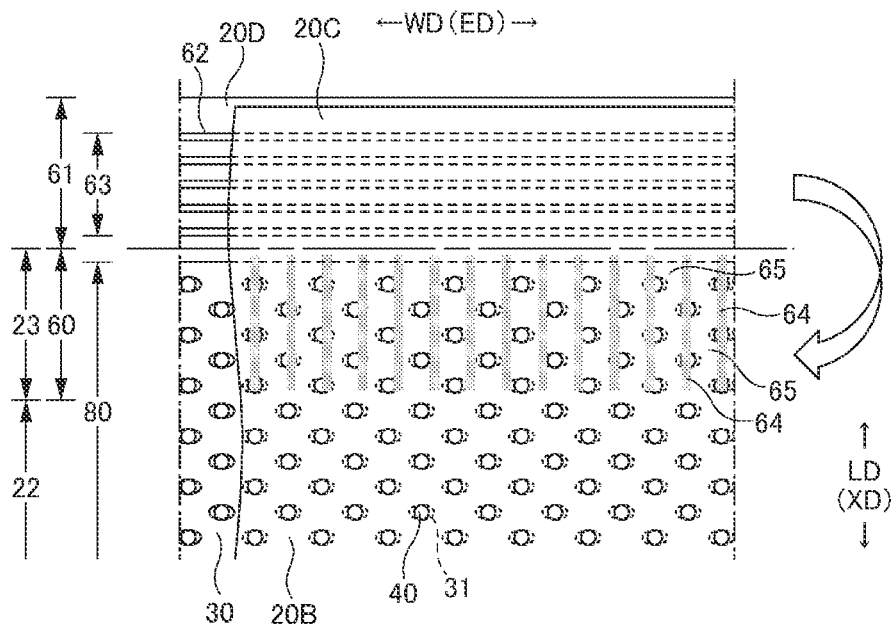
FIG. 19(a) is a plan view of a main part of an outer side portion and an inner side portion in the spread state before these side portions are joined with each other.
FIG. 19(b) is a cross-sectional view passing through an inner/outer bonded portion.
FIG. 19(c) is a cross-sectional view passing through an inner/outer non-bonded portion.
Figure 19:
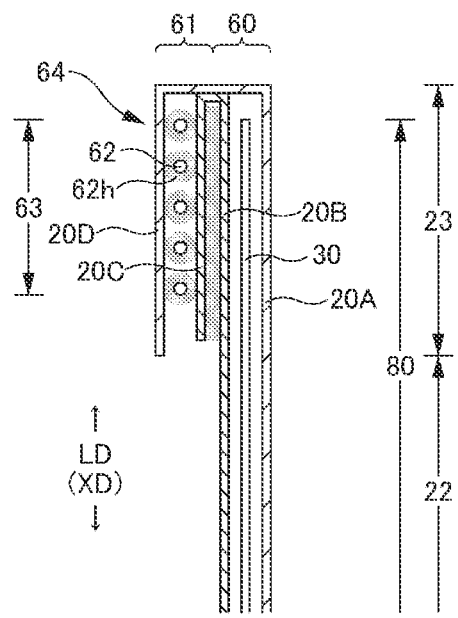
Figure 19:
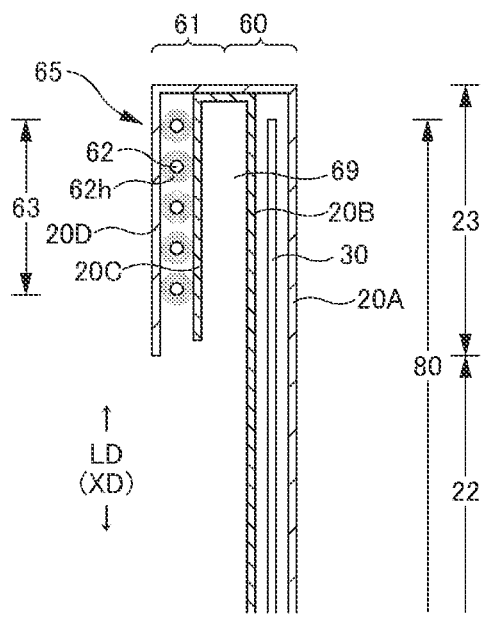

As in the example illustrated in FIG. 4 and the example illustrated in FIG. 19, the waist portion 23 has an inner side portion 61, which is overlapped with an inner side of the outer side portion 60, and, which is joined with the outer side portion 60. The inner side portion 61 is desirably to be provided over the entire waist portion 23 in the width direction WD, but may be provided only in a part of the waist portion 23 in the width direction WD. The dimension in the front-back direction LD of the inner side portion 61 is equal to the dimension in the front-back direction LD of the waist portion 23.

(Inner Side Stretchable Region)

Further, the inner side portion 61 shown in the example illustrated in FIG. 19 includes: a third sheet layer 20C made of a nonwoven fabric; a fourth sheet layer 20D made of a nonwoven fabric; inner side elastic member 62 interposed therebetween; and an inner side stretchable region 63 which contracts in the width direction WD by contraction of the inner side elastic member and is extensible in the width direction WD. The inner side stretchable region 63 is desirably provided over the entire waist portion 23 in the width direction WD, but may be provided only in a part of the waist portion 23 in the width direction WD. In this way, the waist portion 23 has not only the outer side elastic film 30 in the outer side portion 60 but also the inner side elastic member 62 in the inner side portion 61, which means that the waist portion 23 has a dual structure of elastic member (the outer side elastic film 30 and the inner side elastic member 62). This makes easily the tightening force applied to the waist portion 23 stronger than the tightening force applied to the waist adjacent portion 22.

Figure 23:
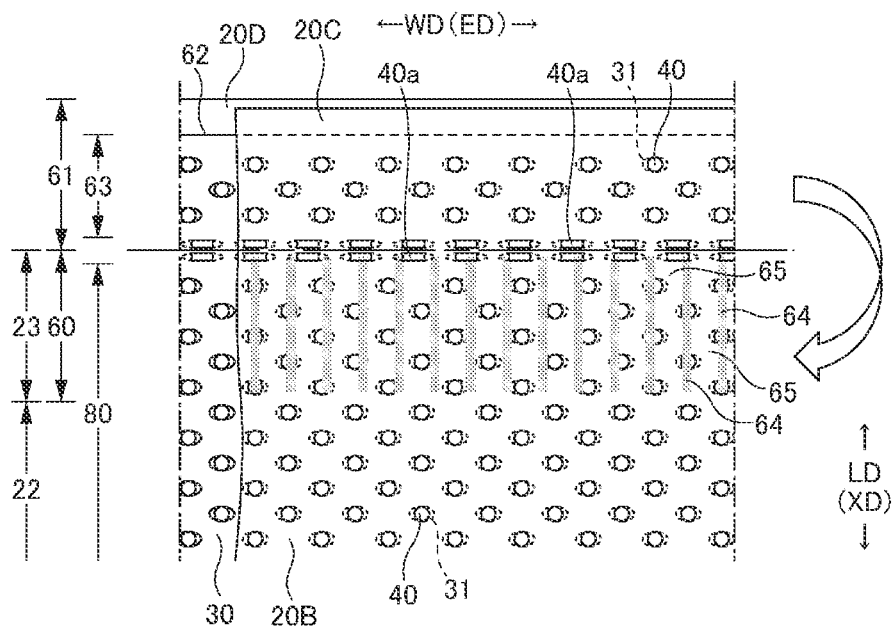
FIG. 23(a) is a plan view of a main part of an outer side portion and an inner side portion in the spread state before these side portions are joined with each other.
FIG. 23(b) is a cross-sectional view passing through an inner/outer bonded portion.
FIG. 23(c) is a cross-sectional view passing through an inner/outer non-bonded portion.
Figure 23:
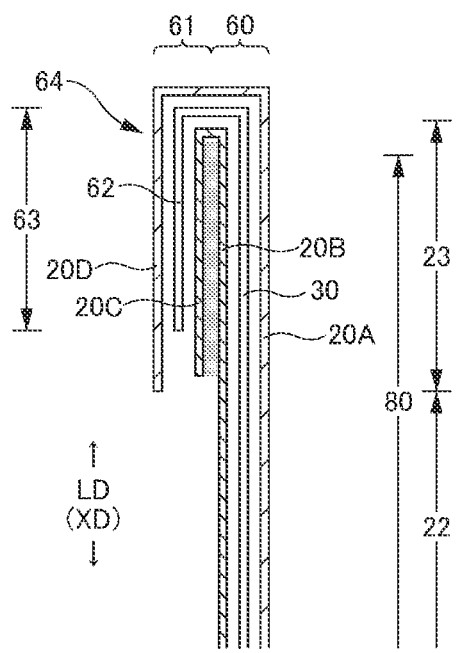
Figure 23:
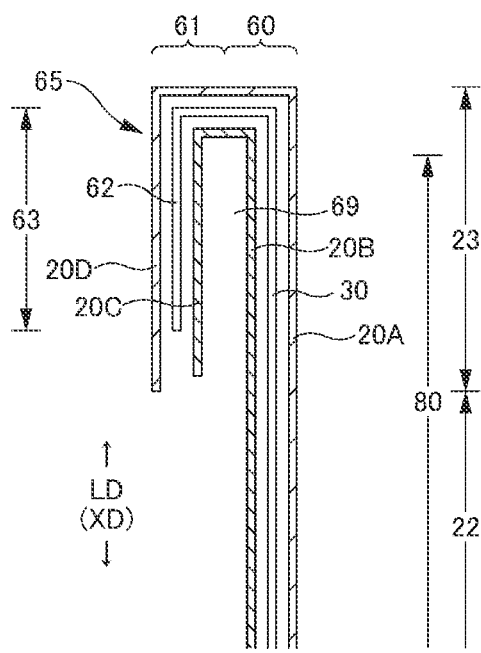

As the inner side elastic member 62, as in the example illustrated in FIG. 19, an elongated elastic member such as a rubber thread may preferably be used. As the elongated elastic member, a spandex rubber thread having the fineness of about 310 to 940 dtex may be used. In addition, when the elongated elastic member is used, it is preferable that a plurality of (e.g., about 3 to 5) elongated elastic members is arranged at intervals (e.g., about 5 to 9 mm) in the front-back direction LD. As explained after, as the inner side elastic member 62, as shown in FIG. 23, an elastic film may be used, but in such a case, the air permeability in the thickness direction of the inner side portion 61 will be inevitably lowered, the improvement of the air permeability by ventilation passages 69 which will be explained after is thereby obstructed as well. Therefore, it is preferable that the plurality of elongated elastic members arranged at intervals is used as the inner side elastic member 62, as shown in FIG. 19 and the like.

As the inner side elastic member 62, as shown in FIG. 23, an elastic film may be used. In this case, the inner side elastic member (inner side elastic film) 62 similar to the outer side elastic film 30 may be used. In this case, each of the inner side elastic member 62 and the outer side elastic film 30 may be a single sheet of a film obtained by folding the sheet at an edge of the waist portion 23, or may be individual two films being discontinuous at the edge of the waist portion 23. Further in this case, it is preferable that a bonding structure of the third sheet layer and the fourth sheet layer 20D in the inner side portion 61 is the same as a bonding structure of the first sheet layer and the second sheet layer 20B in the outer side portion 60 (that is, the third sheet layer 20C and the fourth sheet layer 20D are welded through the joint holes 31 penetrating the inner side elastic member (inner side elastic film) 62.) However, a bonding structure different from the bonding structure of the first sheet layer and the second sheet layer 20B in the outer side portion 60 may be possible.

As shown in FIG. 19 and the like, the third sheet layer 20C and the fourth sheet layer 20D may be individual two nonwoven fabrics. Alternatively, as in the example illustrated in FIG. 24, a single nonwoven fabric is folded back such that a portion at one side and a portion at the other side with respect to a fold line as a boundary refer to the third sheet layer 20C and the fourth sheet layer 20D, respectively. Further, as shown in FIG. 19, a single nonwoven fabric is folded back such that a portion at one side and a portion at the other side with respect to a fold line as a boundary refer to the third sheet layer 20C of the inner side portion 61 and the second sheet layer 20B of the outer side portion 60, respectively. In addition to or instead of this, as shown in FIG. 19, a single nonwoven fabric is folded back such that a portion at one side and a portion at the other side with respect to a fold line as a boundary refer to the fourth sheet layer 20D of the inner side portion 61 and the first sheet layer 20A of the outer side portion 60, respectively.

Figure 22:
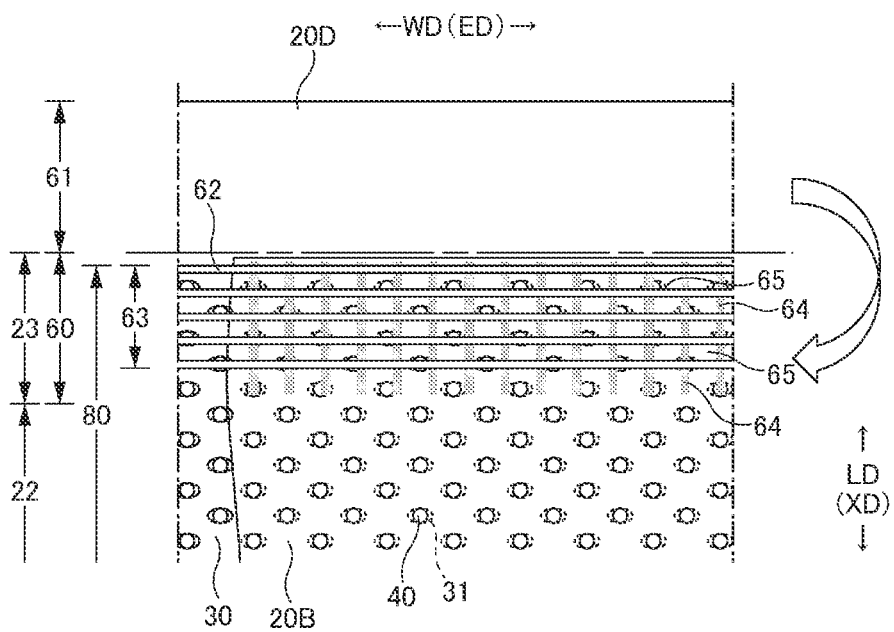
FIG. 22(a) is a plan view of a main part of an outer side portion and an inner side portion in the spread state before these side portions are joined with each other.
FIG. 22(b) is a cross-sectional view passing through an inner/outer bonded portion.
FIG. 22(c) is a cross-sectional view passing through an inner/outer non-bonded portion.
Figure 22:
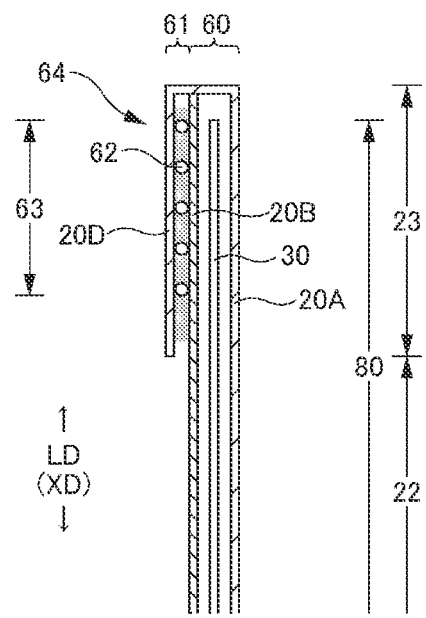
Figure 22:
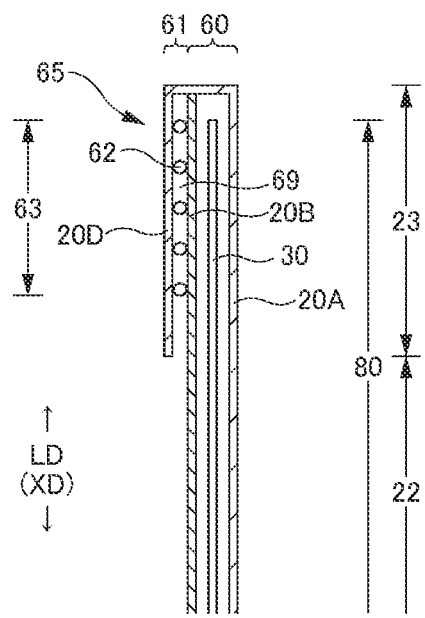

Further, as shown in the example illustrated in FIG. 22, it is preferable that the inner side elastic member 62 is an elongated elastic member; the third sheet layer 20C is used also as the second sheet layer 20B; the inner side elastic member 62 is adjacent to an internal surface of the outer side portion 60; and the inner side elastic member 62 is interposed between the second sheet layer 20B and the fourth sheet layer (cover layer) 20D, because the number of sheet layers may be thereby decreased in the inner side portion 61, so that the air permeability of the waist portion 23 in the thickness direction may be improved.

The third sheet layer 20C and the fourth sheet layer 20D may be continuously bonded to each other in both of the front-back direction LD and the width direction WD, or may be intermittently bonded to each other at least in one of these two directions. In addition, for fixing the inner side elastic member 62 to the third sheet layer 20C and to the fourth sheet layer 20D, the inner side elastic member 62 may have fixing portions at least at both end portions in the width direction WD thereof. Alternatively, the inner side elastic member 62 may have fixing portions provided intermittently or may have a fixing portion provided over entirely in the width direction thereof. In particular, when the inner side elastic member 62 is an elongated elastic member as in the illustrated example, the elongated elastic member may be fixed to the third sheet layer 20C and to the fourth sheet layer 20D through a hot melt adhesive 62h provided only at positions through which the elongated elastic member passes. By doing so, fixing of the elongated elastic member and bonding of the third sheet layer 20C and the fourth sheet layer 20D can be attained simultaneously.

It is preferable that the maximum elongation in the width direction WD of the inner side stretchable region 63 is equal to the maximum elongation in the width direction WD of the outer side stretchable region 80, because between the outer side portion 60 and the inner side portion 61, the dimensions in the width direction WD of components become equal to each other and these components may be produced easily, but the maximum elongation in the width direction WD of the inner side stretchable region 63 may be 0.3 to 1.0 times the maximum elongation in the width direction WD of the outer side stretchable region 80. When the inner side elastic member 62 is an elongated elastic member, the maximum elongation in the width direction WD of the inner side stretchable region 63 can be adjusted by the stretch rate of the inner side elastic member 62 at the time of manufacture. When the inner side elastic member 62 is an elastic film, the maximum elongation in the width direction WD of the inner side stretchable region 63 can be, as in the case of the outer side stretchable region 80, adjusted by the stretch rate of the outer side elastic film 30 at the time of manufacture and factors that inhibit contraction in the width direction WD (such as the length of the sheet joined portion 40).

(Joining of Outer Side Portion and Inner Side Portion in Stripe Pattern)

As shown in FIG. 19, FIG. 20 and the like, the outer side portion 60 and the inner side portion 61 are joined with each other in a stripe pattern formed by disposing, alternately and repeatedly in the width direction WD, the inner/outer bonded portions 64 and the inner/outer non-bonded portions 65 both of which are continuous in the front-back direction LD. This joining can be performed with a hot melt adhesive as shown in the illustrated example, or it can be performed by welding such as ultrasonic welding.

A dimension in the width direction WD of the inner/outer bonded portion 64 can be determined as appropriate, and preferably be about 5 to 10 mm. A dimension in the front-back direction LD of the inner/outer bonded portion 64 can be about 0.9 times to 1 time a dimension in the front-back direction LD of the inner side portion 61. A plurality of inner/outer bonded portions 64 can be arranged intermittently also in the front-back direction LD (at intervals in the front-back direction LD at each of positions in the width direction WD). A dimension in the width direction WD of the inner/outer non-bonded portion 65 (interval in the width direction WD of the inner/outer bonded portions 64) can be determined as appropriate, and preferably be about 10 to 20 mm.

(Relation Between Natural Length of Outer Side Portion and Natural Length of Inner Side Portion)

Characteristically, a natural length in the width direction WD of the outer side portion 60 is preferably set to be 1.1 to 1.8 times, more preferably 1.3 to 1.6 times a natural length in the width direction WD of the inner side portion 61. Note that the natural length in the width direction WD of the outer side portion 60 and the natural length in the width direction WD of the inner side portion 61 are measured in a state where the outer side portion 60 and the inner side portion 61 are peeled off from each other, and in addition, the outer side portion 60 and the inner side portion 61 are separated from each other (cut as necessary).

In this way, the outer side portion 60 and the inner side portion 61 are joined with each other in the stripe pattern, and in addition, the natural length in the width direction WD of the outer side portion 60 is 1.1 to 1.8 times the natural length in the width direction WD of the inner side portion 61, thus, in the worn state including the natural length state of being contracted to some extent, as schematically shown in FIG. 20, in each of the inner/outer non-bonded portions 65, the outer side portion 60 is lifted from the inner side portion 61 to form a ventilation passage 69 continuous in the front-back direction LD between the outer side portion and the inner side portion. Therefore, due to the presence of these ventilation passages 69, air permeability of the waist portion 23 is improved comparing with a case in which the waist portion 23 has merely the dual structure of elastic member.

When the maximum elongation in the width direction WD of the outer side portion 60 is equal to the maximum elongation in the width direction WD of the inner side portion 61, by causing the inner side portion 61 to contract more than the outer side portion 60, a natural length in the width direction WD of the outer side portion 60 can be made longer than a natural length in the width direction WD of the inner side portion 61. In a stretchable structure by an elastic film as in the outer side portion 60, the natural length in the width direction WD can be adjusted by the area ratio of the sheet joined portions 40.

The area ratio of the sheet joined portions 40 to the outer side portion 60 may be the same between the inner/outer non-bonded portions 65 and the inner/outer bonded portions 64. However, as for a natural length in the width direction WD of the outer side portion 60, two cases are assumed: a former case where an area ratio of the sheet joined portions 40 to the outer side portion 60 in the inner/outer non-bonded portions 65 is higher than that in the inner/outer bonded portions 64; and a latter case where these area ratios are equal to each other. Even if a natural length in the width direction WD of the entire outer side portion 60 is the same between the former case and the latter case, a natural length in the width direction WD of the outer side portion 60 in the inner/outer non-bonded portions 65 becomes longer in the former case comparing with the latter case. That is, in each of the inner/outer non-bonded portions 65, the outer side portion 60 is likely to lift more highly from the inner side portion 61.

Meanwhile, the outer side portion 60 and the inner side portion 61 are preferred to include a folded member extending from the outer side portion 60, being folded back at an edge of the waist portion 23, and reaching the inner side portion 61, because in manufacturing, a simple method may be employed in which after the outer side portion 60 and the inner side portion 61 are formed integrally as a member in a state of being flat, this member is folded back at a boundary between the outer side portion and the inner side portion, and then, these side portions are joined with each other. For example, in the example illustrated in FIG. 19 and the like, the folded member here includes a nonwoven fabric (a first nonwoven fabric) forming the first sheet layer 20A and the fourth sheet layer 20D; and a nonwoven fabric (a second nonwoven fabric) forming the second sheet layer 20B and the third sheet layer 20C. Further, in the example illustrated in FIG. 23, the folded member here includes also an elastic film in addition to the first nonwoven fabric and the second nonwoven fabric. However, in this case, one end of each of the above mentioned ventilation passages 69 formed in the worn state between the outer side portion 60 and the inner side portion 61 is blocked by the folded member. Accordingly, even though the air permeability in the thickness direction of the folded member is remained, the improvement of the air permeability is certainly lowered.

In particular, when the folded member includes the elastic film, although the elastic film has air permeability in the thickness direction by the joint holes 31, the air permeability through ventilation passages are inevitably lowered.

Figure 21A:
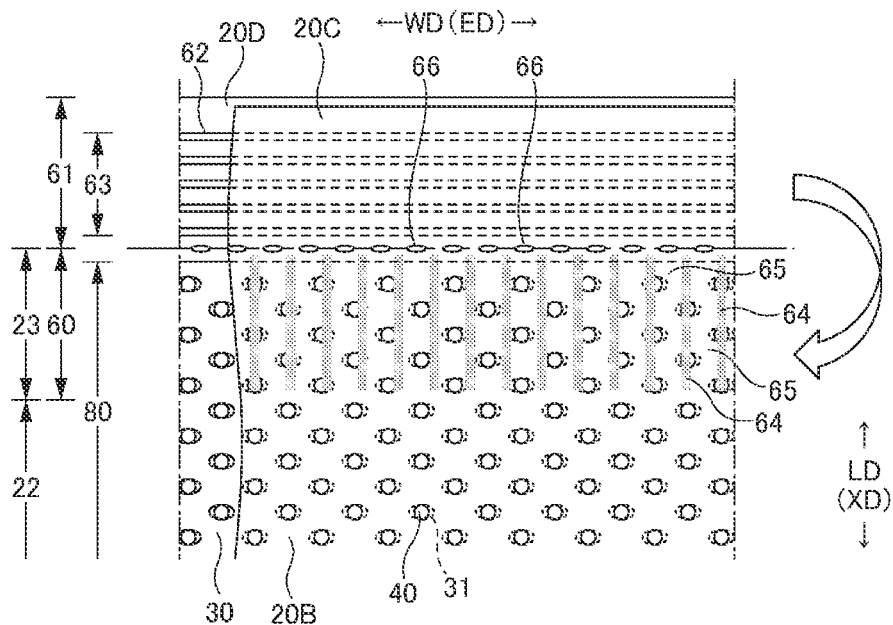
FIG. 21(a) is a plan view of a main part of an outer side portion and an inner side portion in the spread state before these side portions are joined with each other.
Figure 21:
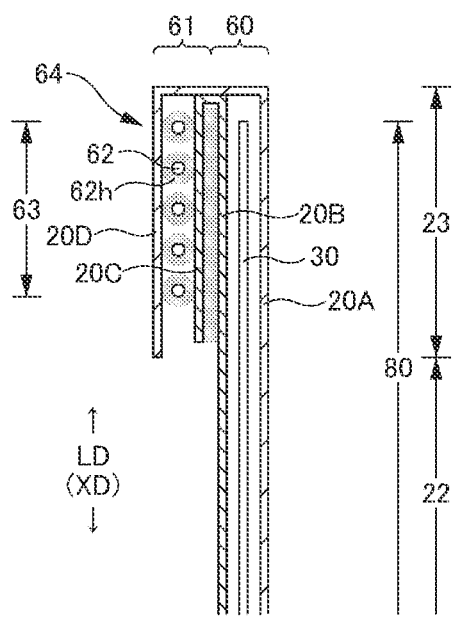
FIG. 21(b) is a cross-sectional view passing through an inner/outer bonded portion.
FIG. 21(c) is a cross-sectional view passing through an inner/outer non-bonded portion.
Figure 21:
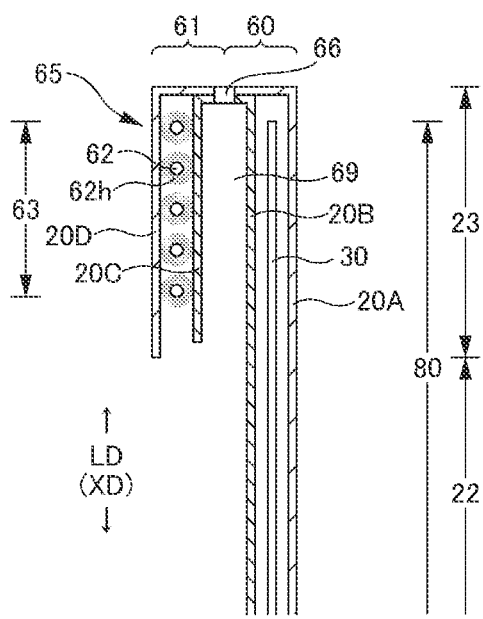

Therefore, as shown in FIG. 21, it is preferable that the vent holes 66 penetrating through the folded member in the thickness direction are formed at intersecting portions of a fold line of the folded member and the inner/outer non-bonded portions 65, respectively. In this way, the above mentioned ventilation passages 69 formed in the worn state between the outer side portion 60 and the inner side portion 61 may communicate with the exterior through the vent holes 66 formed on the edge of the waist portion in the folded member, so that particularly excellent air permeability can be obtained. Note that the vent hole 66 refers to a hole formed by machine processing such as needle sticking, punching, or the like and does not refer to a gap which exists inherently between adjacent fibers in a nonwoven fabric. Further, the vent hole 66 has a longer diameter than that of the gap formed between the adjacent fibers.

In addition, as shown in FIG. 19 and the like, it is also preferable that the folded member does not include the elastic film extending from the outer side portion 60, being folded back at the edge of the waist portion 23, and reaching the inner side portion 61. In this way, since the folded member does not have the elastic film at a site for being folded back, one end of the above mentioned ventilation passage 69 is advantageously not to be blocked by the elastic film. For the similar reason, it is preferable that the folded member does not have a hot melt adhesive at the site for being folded back. In order to make the one end of the ventilation passage 69 open at the edge of the waist portion, a structure is possible in which the folded member is not provided as shown in the example illustrated in FIG. 24.

Further, as in the example illustrated in FIG. 23, it is preferable that the folded member has, in a range extending over the outer side portion 60 and the inner side portion 61, the first nonwoven fabric, the second nonwoven fabric and the elastic film interposed therebetween, and the first nonwoven fabric and the second nonwoven fabric are welded through joint holes 31 penetrating the elastic film at sheet joined portions 40 arranged at intervals to form a layered body as the folded member, because a simple method may be employed in which after not only the outer side portion 60 of the waist portion 23 and the adjacent portion 22 being adjacent to the waist portion 23, but also the inner side portion 61 of the waist portion 23 are formed integrally as a single layered body in a state of being flat, the layered body is folded back such that the inner side portion 61 is inside the outer side portion 60, and then, these side portions are joined with each other. However in such a case, when the sheet joined portions 40 are disposed on the fold line of the folded member, the edge of the waist portion 23 disadvantageously becomes hard in the texture thereof. In addition, since the folded member is likely to bend along an edge of each of the sheet joined portions 40, it becomes difficult to stabilize the fold position in the folded member.

Therefore, in this case, as in the example illustrated in FIG. 23, it is preferable that the sheet joined portions 40 are not disposed on the fold line of the folded member, and intervals in the width direction WD of sheet joined portions 40a adjacent to an outer side of the fold line of the folded member and intervals in the width direction WD of sheet joined portions 40a adjacent to an inner side of the fold line of the folded member are narrower than intervals in the width direction WD of other sheet joined portions 40. In this case, since the sheet joined portions are not disposed on the fold line, the edge of the waist portion 23 does not become hard in the texture thereof, and in addition, the fold position (based on alternate long and short lines illustrated in drawings) of the folded-member can bestabilized.

<Description of Terms in Specification>

The following terms in the specification have the following meanings unless otherwise specified in the specification.

The "front body" and the "back body" refer to portions on the front side and the back side, respectively, with respect to a center of the underpants-type disposable diaper in the front-back direction as a boundary. In addition, the crotch portion refers to a range in the front-back direction including the center of the underpants-type disposable diaper in the front-back direction, and refers to a range of a portion having a narrowing portion in the front-back direction when the absorbent body has the narrowing portion.

The "maximum elongation" refers to a maximum value of an elongation in the stretchable direction ED (in other words, an elongation in the flatly spread state without contraction (including any kinds of contraction such as contraction by an elastic member) or slack), and represents a length in the spread state as a percentage when the natural length is 100%.

The "area ratio" refers to a ratio of a target portion to a unit area, and is represented as a percentage by dividing a total area of target portions (for example, the sheet joined portions 40, the openings of the joint holes 31, and the vent holes) in target regions (for example, the outer side stretchable region 80 and the non-stretchable region 70) by an area of the target regions. In particular, the "area ratio" in a region having the stretchable structure refers to an area ratio in the spread state. In a mode in which a plurality of target portions is provided at intervals, it is desirable to obtain the area ratio by setting a size of the target regions to include ten or more target portions.

The "stretch rate" refers to a value when the natural length is 100%. For example, a stretch rate of 200% is synonymous with an elongation ratio of 2.

The "basis weight" is measured as below. A sample or a test piece is pre-dried, and then is left in a test room or a device in a standard state (temperature 23±1° C., relative humidity 50±2% in a test location), and is put in a constant weight state. Pre-drying refers to setting the weight of the sample or the test piece to a constant weight in an environment in which temperature is 100° C. Incidentally, pre-drying is unnecessary for a fiber having an official moisture regain of 0.0%. A sample having dimensions of 100 mm×100 mm is cut off from the test piece in the constant weight state using a sampling template (100 mm×100 mm). A weight of the sample is measured and multiplied by 100 to calculate a weight per square meter, and the weight is set to the basis weight.

The "thickness" of the absorbent body is measured using a thickness measuring instrument of Ozaki Mfg. Co., Ltd. (Peacock, Dial Thickness Gauge Large Type, Model J-B (measurement range 0 to 35 mm) or Model K-4 (measurement range 0 to 50 mm)) by horizontally placing the sample and the thickness measuring device. A "thickness" other than the above thickness is automatically measured under the condition of load: 0.098 N/cm$^2$ and pressure area: 2 cm$^2$ using an automatic thickness meter (KES-G5 handy compression measurement program).

The "tensile strength" and the "tensile elongation (breaking elongation)" refer to values measured by setting an initial chuck interval (distance between marked lines) to 50 mm and a tensile speed to 300 mm/min in accordance with JIS K7127: 1999 "Plastics-Determination of tensile properties-" except that the test piece has a rectangular shape of width 35 mm×length 80 mm. As a tensile testing machine, for example, AUTOGRAPH AGS-G100N manufactured by SHIMADZU CORPORATION can be used.

The "stretching stress" refers to the tensile stress (N/35 mm) measured when stretching in the elastic region by a tensile test setting an initial chuck interval (distance between marked lines) to 50 mm and a tensile speed to 300 mm/min in accordance with JIS K7127: 1999 "Plastics-Determination of tensile properties-", and a degree of stretching can be appropriately determined depending on the test object. It is preferable that the test piece has a rectangular shape having a width of 35 mm and a length of 80 mm or more. However, when a test piece having a width of 35 mm may not be cut out, the test piece is created to have a width allowing cutting out, and a measured value is set to a value converted to have the width of 35 mm. In addition, even in a case in which the target region is small and sufficient test pieces may not be collected, when the magnitude of stretching stress is compared, even a suitably small test piece can be compared at least as long as test pieces of the same size are used. As a tensile testing machine, for example, AUTOGRAPH AGS-G100N manufactured by SHIMADZU CORPORATION can be used.

The "spread state" refers to a flatly spread state without contraction (including any kinds of contraction such as contraction by an elastic member) or slack.

Dimensions of each portion refer to dimensions in a spread state rather than the natural length state unless otherwise stated.

When there is no description about an environmental condition in a test or measurement, it is presumed that the test or measurement is performed in a test room or a device in a standard state (temperature 23±1° C., relative humidity 50±2% in a test location).

INDUSTRIAL APPLICABILITY

The present invention can be applied to, as long as an elastic member elastically stretching and contracting by an elastic film is provided, general disposable wearing articles such as tape type disposable diapers, disposable wearing articles for swimming or playing in the water, etc. in addition to the underpants-type disposable diapers as in the above example.

REFERENCE SIGNS LIST

10 Inner member
10B Inner/outer fixing region
11 Top sheet
12 Liquid impervious sheet
13 Absorbent body
13N Narrower portion
14 Wrapping sheet
17 Non-absorbent body side portion
20 Outer member
20A First sheet layer
20B Second sheet layer
20C Third sheet layer 20D Fourth sheet layer
20X Elastic film stretchable structure
21 Side seal portion
22 Waist adjacent portion
23 Waist portion
25 Contraction pleats
30 Outer side elastic film
31 Joint hole
32 Hole-less band
40, 40a Sheet joined portion
51, 52 Non-joint band
51 First non-joint band
51d First direction
51s First interval
51w First width
52 Second non-joint band
52d Second direction
60 Outer side portion
61 Inner side portion
62 Inner side elastic member
62h Hot melt adhesive
63 Inner side stretchable region
64 Inner/outer bonded portion
65 Inner/outer non-bonded portion
66 Vent hole
69 Ventilation passage
70 Non-stretchable region
80 Outer side stretchable region
90 Three-dimensional gather
93 Fallen portion
94 Free portion
95 Gather sheet
96 Gather elastic member
B Back body
ED Stretchable direction
F Front body
L Intermediate portion
LD Front-back direction
T Lower torso portion
WD Width direction
XD Orthogonal direction

The invention claimed is:

1. A disposable wearing article comprising:
a waist portion having an outer side portion exposed on an external surface and an inner side portion overlapped with an inner side of the outer side portion;
a waist adjacent portion continuing extending from the outer side portion of the waist portion toward a crotch side;
an outer side stretchable region extending over the outer side portion of the waist portion and the waist adjacent portion; and
an inner side stretchable region provided in the inner side portion of the waist portion,
wherein the outer side stretchable region has
a first sheet layer made of a nonwoven fabric,
a second sheet layer made of a nonwoven fabric, and
an outer side elastic film being interposed therebetween and extending over the outer side portion of the waist portion and the waist adjacent portion,
the first sheet layer and the second sheet layer are welded through joint holes penetrating the outer side elastic film at sheet joined portions arranged at intervals,
the outer side stretchable region contracts in a width direction by contraction of the outer side elastic film and is extensible in the width direction,
the inner side stretchable region includes an inner side elastic member,
the inner side stretchable region contracts in the width direction by contraction of the inner side elastic member and is extensible in the width direction,
the outer side portion and the inner side portion are joined with each other in a stripe pattern formed by disposing, alternately and repeatedly in the width direction, inner/outer bonded portions continuous in a front-back direction and inner/outer non-bonded portions continuous in the front-back direction, and
a natural length in the width direction of the outer side portion is 1.1 to 1.8 times a natural length in the width direction of the inner side portion.

2. The disposable wearing article according to claim 1, further comprising a folded member extending from the outer side portion, being folded back at an edge of the waist portion, and reaching the inner side portion,
wherein vent holes penetrating through the folded member in a thickness direction thereof are formed at intersecting portions of a fold line of the folded member and the inner/outer non-bonded portions, respectively.

3. The disposable wearing article according to claim 1, further comprising a folded member extending from the outer side portion, being folded back at an edge of the waist portion, and reaching the inner side portion,
wherein the folded member does not include the elastic film extending from the outer side portion, being folded back at the edge of the waist portion, and reaching the inner side portion.

4. The disposable wearing article according to claim 1, wherein the inner side elastic member is formed of a plurality of elongated elastic members continuous in the width direction and arranged at intervals in the front-back direction.

5. The disposable wearing article according to claim 4, wherein the inner side portion has the inner side elastic member being adjacent to an internal surface of the outer side portion and a cover layer made of a nonwoven fabric for covering an inner side of the inner side elastic member, and
the internal surface of the outer side portion and an external surface of the cover layer of the inner side portion are joined with each other in the stripe pattern.

6. The disposable wearing article according to claim 1, further comprising a folded member extending from the outer side portion, being folded back at an edge of the waist portion, and reaching the inner side portion,
wherein the folded member has, in a range extending over the outer side portion and the inner side portion, a first nonwoven fabric, a second nonwoven fabric and an elastic film interposed therebetween,
the first nonwoven fabric and the second nonwoven fabric are welded through joint holes penetrating the elastic film at sheet joined portions arranged at intervals to form a layered body as the folded member,
a portion of the first nonwoven fabric, a portion of the second nonwoven fabric and a portion of the elastic film, which are located in the outer side portion, form the first sheet layer, the second sheet layer and the outer side elastic film, respectively,
a portion of the elastic film, which is located in the inner side portion, forms the inner side elastic member,
the sheet joined portions are not disposed on a fold line of the folded member, and intervals in the width direction of sheet joined portions adjacent to an outer side of the fold line of the folded member and intervals in the width direction of sheet joined portions adjacent to an inner side of the fold line of the folded member are narrower than intervals in the width direction of other sheet joined portions.

7. The disposable wearing article according to claim 1,
wherein a maximum elongation in the width direction of the outer side portion is equal to a maximum elongation in the width direction of the inner side portion, and
an area ratio of the sheet joined portions to the outer side portion in the inner/outer non-bonded portions is larger than an area ratio of the sheet joined portions to the outer side portion in the inner/outer bonded portions.

8. The disposable wearing article according to claim 1,
wherein the wearing article is an underpants-type disposable wearing article including
   an integrated outer member from a front body to a back body or outer members separately provided for the front body and the back body,
   an inner member attached to an intermediate portion of the outer member in a width direction, the inner member extending to both front and back sides of a crotch portion,
   side seal portions in which both side portions of the outer member in the front body and both side portions of the outer member in the back body are bonded to each other, respectively, and
   a waist opening and a pair of right and left leg openings,
wherein the outer member includes the waist portion and the waist adjacent portion.

* * * * *